US010737106B2

(12) United States Patent
Turner et al.

(10) Patent No.: US 10,737,106 B2
(45) Date of Patent: *Aug. 11, 2020

(54) APPARATUS AND METHOD FOR CREATING SMALL FOCUS DEEP HYPERTHERMIA IN TISSUES OF THE BRAIN

(71) Applicant: Pyrexar Medical Inc., Salt Lake City, UT (US)

(72) Inventors: Paul F. Turner, Bountiful, UT (US); Jason Ellsworth, Farmington, UT (US)

(73) Assignee: Pyrexar Medical Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/973,472

(22) Filed: May 7, 2018

(65) Prior Publication Data

US 2019/0030354 A1 Jan. 31, 2019

Related U.S. Application Data

(63) Continuation-in-part of application No. 14/706,909, filed on May 7, 2015, now Pat. No. 10,039,926.

(Continued)

(51) Int. Cl.
*A61N 1/40* (2006.01)
*A61N 2/02* (2006.01)
(Continued)

(52) U.S. Cl.
CPC .......... *A61N 1/406* (2013.01); *A61K 41/0052* (2013.01); *A61N 1/403* (2013.01);
(Continued)

(58) Field of Classification Search
CPC ... A61N 5/025; A61N 5/027; A61N 2005/027
See application file for complete search history.

(56) References Cited

U.S. PATENT DOCUMENTS

| 4,672,980 A | 6/1987 | Turner |
| 5,097,844 A | 3/1992 | Turner |

(Continued)

OTHER PUBLICATIONS

Gellermann et al.; "Simulation of Different Applicator Positions for Treatment of a Presacral Tumour"; International Journal on Hyperthermia; (Feb. 2007); pp. 37-47; vol. 23, No. 1.

(Continued)

*Primary Examiner* — Kaitlyn E Smith
(74) *Attorney, Agent, or Firm* — Thorpe North and Western, LLP

(57) ABSTRACT

A radio frequency annular phased array hyperthermia system providing a heated focal zone with a diameter of 3 cm or less in a tissue mass includes a plurality of at least 42 radio frequency energy applicators in three rings adapted to surround the tissue mass. A bolus having a dielectric constant is positioned between the energy applicators and the tissue mass. The energy applicators operate at a frequency of at least about 900 MHz. to create the heated focal zone. The circumferential spacing between adjacent applicators in each ring is less than a critical distance and spacing between adjacent side by side rings is also less than a critical distance with such critical distances being interdependent on the frequency of the energy radiated, the dielectric constant of the bolus, the size of the bolus, and the size of the tissue mass.

18 Claims, 27 Drawing Sheets

Related U.S. Application Data

(60) Provisional application No. 61/990,036, filed on May 7, 2014.

(51) Int. Cl.
*A61N 2/00* (2006.01)
*A61N 5/04* (2006.01)
*A61K 41/00* (2020.01)

(52) U.S. Cl.
CPC ............... *A61N 2/006* (2013.01); *A61N 2/02* (2013.01); *A61N 5/045* (2013.01)

(56) References Cited

U.S. PATENT DOCUMENTS

| | | | |
|---|---|---|---|
| 5,503,150 A | 4/1996 | Evans | |
| 5,540,737 A | 7/1996 | Fenn | |
| 7,123,010 B2* | 10/2006 | Krockel | A61N 1/403 324/318 |
| 10,039,926 B2* | 8/2018 | Turner | A61N 1/403 |
| 2004/0044385 A1 | 3/2004 | Fenn et al. | |
| 2009/0306646 A1 | 12/2009 | Turner et al. | |
| 2011/0245900 A1 | 10/2011 | Turner et al. | |
| 2012/0172954 A1 | 7/2012 | Zastrow et al. | |
| 2014/0012063 A1 | 1/2014 | Turner et al. | |

OTHER PUBLICATIONS

Paulsen et al.; "Optimization of Pelvic Heating Rate Distributions with Electromagnetic Phased Arrays"; International Journal on Hyperthermia; (1999); pp. 157-186; vol. 15, No. 3.

Seebass et al.; "Electromagnetic Phased Arrays for Regional Hyperthermia: Optimal Frequency and Antenna Arrangement"; International Journal on Hyperthermia; (2001); pp. 321-336; vol. 17, No. 4.

Wust et al.; "3-D Computation of E Fields by the Volume-Surface Integral Equation (VSIE) Method in Comparison with the Finite-Integration Theory (FIT) Method"; IEEE Trans Biomed Eng.; (Aug. 1993); pp. 745-759; vol. 40, No. 8.

Wust et al.; "Antenna Arrays in the SIGMA-Eye Applicator: Interactions and Transforming Networks"; Medical Physics; (Aug. 2001); pp. 1793-1805; vol. 28, No. 8.

Wust et al.; "Electric Field Distributions in a Phased-Array Applicator with 12 Channels: Measurements and Numerical Simulations"; Medical Physics; (Nov. 2000); pp. 2565-2579; vol. 27, No. 11.

Adibzadeh et al.; "Absence of Acute Ocular Damage in Humans after Prolonged Exposure to Intense RF EMF"; Physics in Medicine & Biology; (Dec. 18, 2015); pp. 488-503; vol. 61; <doi: 10.1088/0031-9155/61/2/488 >.

Cohen et al.; *Memory, Amnesia, and the Hippocampal System*; [Overview]; (Oct. 1993); 326 pages; The MIT Press; <ISBN: 9780262032032 >.

Franklin et al.; "The Role of Heat Shock Proteins Hsp70 and Hsp27 in Cellular Protection of the Central Nervous System"; International Journal of Hyperthermia; (Sep. 2005); pp. 379-392; vol. 21, No. 5; <doi: 10.1080/02656730500069955 >.

Murphy; "Amyloid-Beta Solubility in the Treatment of Alzheimer's Disease"; The New England Journal of Medicine; (2018); pp. 391-392; vol. 378, No. 4; <doi: 10.1056/NEJMe1714638 >.

Salford et al.; "Effects of Electromagnetic Fields From Wireless Communication upon the Blood-Brain Barrier"; In: BioInitiative 2012; (Sep. 2012); 52 pages; Section10.

Smith et al.; "Stress Proteins in Alzheimer's Disease"; International Journal of Hyperthermia; (Aug. 2005); pp. 421-431; vol. 21, No. 5; <doi: 10.1080/02656730500133165 >.

Wang et al.; "Heat Shock Proteins at the Crossroads Between Cancer and Alzheimer's Disease"; BioMed Research International; (2014); 9 pages; vol. 2014, Article ID 239164; <doi: 10.1155/2014/239164 >.

Zastrow et al.; "Time-Multiplexed Beamforming for Noninvasive Microwave Hyperthermia Treatment"; IEEE Transactions on Biomedical Engineering; (Jun. 2011); pp. 1574-1584; vol. 58, No. 6; <doi: 10.1109/TBME.2010.2103943 >.

\* cited by examiner

APPARATUS AND METHOD FOR CREATING SMALL FOCUS DEEP HYPERTHERMIA IN TISSUES OF THE BRAIN

RELATED APPLICATIONS

This is a continuation-in-part of application Ser. No. 14/706,909, now U.S. Pat. No. 10,039,926, filed May 7, 2015, entitled Apparatus and Method for Creating Small Focus Deep Hyperthermia in Tissue, which claimed priority to U.S. Provisional Patent Application Ser. No. 61/990,036 filed May 7, 2014, both of which are hereby incorporated herein by reference.

BACKGROUND OF THE INVENTION

Field

The present invention relates generally to systems and apparatus for irradiating targets with electromagnetic radiation, and more specifically to systems having annular-type or various sectored applicators and associated control systems for controlling application of radiation to targets through phased array power steering and particularly to focus electromagnetic radiation (EMR) energy in target tissues of the brain.

State of the Art

Current systems for applying electromagnetic radiation (EMR) to targets, such as living bodies and biological tissue, and controlling the position of a region of heating within the target through phased array power steering are provided with a plurality of electromagnetic applicators powered by multi-channel EMR systems where different applicators are each provided with electronically controlled power and electronically controlled phase for different channels of the EMR system. This creates a desired phased array heat pattern steering capability.

Several types of therapeutic treatments for cancer in humans are in current, common use. These treatments include surgery, X-rays, radiation from particle accelerators and radioactive sources, and chemotherapy. These treatments are often combined in various ways to enhance treatment effectiveness.

Although such conventional treatment techniques have been successful in treating cancer in many patients and in prolonging the lives of many other patients, they are frequently ineffective against many types of cancer and often have severe adverse side effects at the necessary treatment levels. Protracted treatment of cancer patients by X-rays or chemotherapy, as an example, tends to eventually destroy or inhibit the patients' natural immunological systems to an extent that many patients eventually succumb to common infectious diseases, such as influenza or pneumonia, which otherwise probably would not be fatal. Also, many patients having advanced stages of cancer or complications may become too weak to withstand the trauma of surgical or other cancer treatments so that therapy must be discontinued.

Due both to the prevalence and the typically severe consequences of human cancer, as well as frequent ineffectiveness of current treatments such as those mentioned above, medical researchers are continually experimenting in an attempt to discover and develop improved or alternative cancer treatment methods with their associated treatment apparatus.

Hyperthermia, the generation of artificially elevated body temperatures, has recently been given serious scientific consideration as an alternative means for cancer treatment. Much research has been conducted into the effectiveness of hyperthermia alone or in combination with other treatment methods. This research is important in that hyperthermia techniques appear to have the potential for being extremely effective in the treatment of many or most types of human dancer, without the adverse side effects which are associated with current methods for cancer treatment. Hyperthermia is sometimes called thermal therapy, indicating raising the temperature of a region of the body.

Researchers into hyperthermia treatment of cancer have commonly reported that many types of malignant growths in humans can be thermally destroyed, usually with no serious adverse side effects, by heating the malignancies to temperatures slightly below that which would be injurious to most normal, healthy cells. Furthermore, many types of malignant cell masses have reportedly been found to have substantially lower heat transfer to lessen their ability to dissipate heat, presumably due to poorer vascularity and reduced blood flow characteristics. Consequently, these types of growths appear to be more affected by the hyperthermia treatment, i.e., reach higher temperatures than tissue having normal blood flow. This is referred to as a "therapeutic gain". Poorly vascularized malignant growths can reportedly be heated to temperatures several degrees higher than the temperature reached by the immediately surrounding healthy tissue. This promises to enable hyperthermic treatment of those types of malignant growths which are more thermally sensitive than normal tissue without destruction of normal cells, and additionally to enable higher temperature, shorter hyperthermia treatment times of more thermally sensitive types of malignancies which exhibit poor vascularity.

In this regard, researchers have commonly reported that as a consequence of these thermal characteristics of most malignant growths and the thermal sensitivity of normal body cells, hyperthermia temperatures for the treatment of human, cancer should be carefully limited within a relatively narrow effective and safe temperature range. Hyperthermia is generally provided by temperatures over 40 degrees C. (104 degrees F.). At treatment temperatures above approximately 45 degrees C. (113 degrees F.), thermal damage to most types of normal cells is routinely observed if the time duration exceeds 30 to 60 minutes. Thus, great care must be taken not to exceed these temperatures in healthy tissue for a prolonged period of time. The duration of exposure at any elevated temperature is, of course, an important factor in establishing the extent of thermal damage to the healthy tissue. However, if large or critical regions of the human body are heated above 45 degrees C. for even relatively short times, injury to normal tissue is likely to result. The intent of hyperthermia is to get as much of the tumor region above 40 degree C. as is possible, while not heating the normal tissue above 44 degrees C. If a more selective high temperature can be obtained in the tumor or target tissue, there will be a greater desirable amount of damage done to the tumor or target tissue.

In treating cancerous tissue, it is important to heat all of the cancerous tissue to therapeutic temperatures which can include temperatures well over 45 degrees C., with temperatures over 60 degrees C. desirable in some situations, without heating the normal tissue to temperatures which will injure the normal tissue. Greater tumor or target tissue damage can be obtained at higher temperatures. The goal of most hyperthermia systems is to be able to heat the tissue in need of treatment without heating the normal tissue surrounding the tissue in need of treatment. Therefore, to provide such treatment it is desirable to have a hyperthermia system which can provide a heating zone about the size of the tumor or other diseased tissue to be treated and it is critical to provide this heating zone at the location of the tumor or other diseased tissue to be treated. This can be particularly difficult in treating tumors or other tissue to be treated that is located deep within a relatively large mass of normal tissue, such as within a human torso, i.e., within the pelvis, abdomen, or thorax. The torso of an adult human is typically of a size having diameters between about 22 cm and 33 cm. A tumor or other tissue deposit to be treated in a human pelvis, abdomen, or thorax typically has a maximum diameter of about 8 cm or less and may be located in various positions within the pelvis, abdomen, or thorax. Most of these are located deep within the normal body tissue, as opposed to neat the surface of the normal tissue (skin), and require what is referred to as "deep-heating".

Hyperthermia systems using phased arrays of radio frequency radiating applicators arranged noninvasively around an area of the body containing a tumor or other tissue to be treated, such as the pelvis, abdomen, or thorax, are commercially available. Extensive articles and reports have been written on the use of these phased array systems to provide hyperthermia heat pattern steering, and several patents have been issued covering the use of phased arrays, see, for example, U.S. Pat. Nos. 5,097,844 and 4,672,980. All of these systems rely upon the use of electronic phase and power steering to provide heat pattern focusing and steering control. When radio frequency signals are directed into a body portion from several applicators arranged around the body portion, these signals are superimposed within the body portion to provide areas of constructive interference and areas of destructive interference. The areas of constructive interference are areas of heating with maximum heating occurring where the largest number of superimposed signals constructively interfere. In a phased array hyperthermia system, the phase and amplitude of each signal is chosen so that theoretically all of the signals directed into the body will be superimposed to constructively interfere and provide maximum heating at the location of the tissue to be treated and will form a heated focal zone at that location. This heated focal zone should be of a temperature and size to heat the entire area of tissue to be treated to the desired minimum temperature for treatment while not heating surrounding tissue to an extent to cause damage to this surrounding tissue. As indicated above; it is important to limit the heating of the normal tissue surrounding the tissue to be treated. However, although not preferred, in many instances some destructive heating of normal tissue surrounding the tissue to be treated can be tolerated to ensure that all tissue to be treated is heated to the critical temperature. It is also important that hot spots that could damage normal tissue are not created in areas of normal tissue away from the tissue to be treated or away from the tissue immediately surrounding the tissue to be treated.

The BSD-2000 system produced by Pyrexar Medical Company (formerly produced by BSD Medical Corporation), Salt Lake City, Utah, is a radio frequency annular phased array hyperthermia system for heating deep seated tissue to be treated in a relatively large diameter tissue mass such as a human torso. The system provides three rings of multiple radio frequency applicators, such as radio frequency dipole antennas or radio frequency dipole antenna pairs, with the applicators of each ring spaced around an opening adapted to receive therein the body portion having the tissue to be treated. The respective rings are spaced or stacked along the longitudinal axis of the body portion having the tissue to be treated. Separate power channels control the frequency, radiated power, and relative phase of the radio frequency energy radiated by each applicator or combination of selected applicators. Such a system is described in U.S. Pat. No. 5,097,844. Each channel is connected to an antenna or an antenna pair in the array and has separate electronic controls for the power and phase of the radio frequency signal sent to the connected antenna, antenna pair, or combination of selected antennas or antenna pairs. This allows electronic steering and focusing of the heating pattern. The most advanced phased array applicator configuration currently used with this system is called the "Sigma Eye", and contains three rings of dipole antennas as described in U.S. Pat. No. 5,097,844. However, rather than circular rings as shown in U.S. Pat. No. 5,097,844, the rings of the Sigma Eye applicator are elliptical in shape. The Sigma Eye elliptical rings provide improved comfort for patients over circular rings and maximizes the 3D energy convergence at the targeted treatment location. The use of three rings of applicators allows three dimensional steering and focusing of the heating zone created by the antenna array. U.S. Pat. No. 4,672,980 teaches a system having an antenna array containing two rings of dipole antennas to provide two dimensional-steering and focusing of the heating zone created by that antenna array. It should be noted that in the present application, as shown by the Sigma Eye configuration disclosed, "ring" is not used to mean circular, but to mean a plurality of applicators spaced around an opening adapted to receive a body part so that with a body part received in the opening the applicators of the ring are spaced around the body part in a manner to direct the radio frequency signals into the body part. The rings can take various configurations; which can be, for example, a circular configuration, an elliptical configuration, a rectangular configuration, a triangular configuration, or other configuration surrounding the tissue to be heated. Similarly, while such systems are generally referred to as annular phased array systems, the use of the term "annular" does not limit the system to circular arrays but to arrays having any shape as indicated above for the meaning of ring.

Prior art phased array systems have successfully used radio frequency signals up to 120 MHz to provide deep heating of tissue in the human torso which includes the pelvis, abdomen, and thorax. The commercial BSD-2000 system using the Sigma Eye as described above has been limited to use of radio frequency signals no greater than 100 MHz when used for deep heating. This frequency limit was chosen in order to provide sufficient penetration of the radiation deep into the tissue to provide a controlled heated focal zone deep in the tissue without producing hot spots in other parts of the tissue away from the heating zone. In order to obtain optimum localization of heating at depth it is necessary to use a frequency low enough to have sufficient penetration and limit the formation of standing waves that could produce hot spots in the tissues away from the desired heated focal zone. There is no data indicating that a frequency above 100 MHz can provide an adequate deep central heated focal zone in the relatively large tissue mass of the adult torso. Also, it was expected that the use of higher frequencies would have the potential for creating multiple hot spots within the normal tissue away from the desired heated focal zone due to the standing waves. The current BSD-2000 system uses a maximum operating frequency of 100 MHz for deep body heating and uses 12 RF power and phase control channels to drive 12 pairs of linear dipole antennas as described in U.S. Pat. No. 5,097,844. This system provides deep heating of the pelvic, abdominal, and thorax regions of an adult with a heated focal zone volume of 1,500 to 5,000 cubic centimeters at a frequency of 100 MHz. The 1,500 cc volume corresponds to a primary heating volume with a diameter of 14 cm in each of the three orthogonal axes. However, as indicated above, most target tumors deep in the body are much smaller than this size, typically with a diameter of less than 8 cm. Using frequencies at or below 120 MHz in a noninvasive antenna array system forms a spherical focus for the heated focal zone which has a major axis diameter of 20 cm or greater. When the focus is spheroidal, using frequencies no greater than 120 MHz, it is possible to lessen one dimension to as small as 10 cm, but then the other maximum diameter dimension is greater than 20 cm. This is much larger than the typical size of the tissue needing heat treatment so substantial volumes of normal tissue around the deposit to be treated will also be heated and damaged. The use of higher frequency RF signals can theoretically reduce the size of the heating zone produced by the interacting signals. Some reports have indicated that frequencies as high as 434 MHz have been used with annular type phased array systems for producing smaller heating zones in body parts such as limbs or the neck region of a body. Such high frequencies can be used in these regions due to the much smaller total tissue mass size for these regions of the human body. With these smaller sized body parts, deep tissue penetration is not needed.

While the U.S. Pat. No. 5,097,844 discloses that the theoretical focal zone size can be reduced by using higher frequencies, it does not disclose how such a system could be implemented to provide a small and deep focal zone size and a selectively heated focal zone at depth in the tissue. Further, the patent does not disclose how the deep local heated focal zone could be preserved when phase and amplitude steering is done to direct the smaller heated focal zone to a targeted treatment site. Therefore, there is a need to develop a means to utilize higher operating frequencies to reduce the size of the heated focal zone. To accomplish this requires special design considerations and limitations that were not foreseen or included in U.S. Pat. No. 5,097,844. The higher frequencies have not been used in prior art systems for deep tissue heating. The inventors have found that the use of higher frequencies to enable smaller heated focal zones in deep tissue heating require special design constraints for the annular phased arrays and careful consideration of the bolus interface media between the applicator array and the human body. The dependence of body size, the size of the targeted tissue, the array size, the array shape, the number of radiating applicators, the number of independent RF power and phase control channels, the bolus interface media, and the operating frequency must all be considered in the design in order to achieve a desired selective deep heated focal zone.

The parent application sets forth special design considerations and limitations for an annular phased array hyperthermia system that uses radio frequency signals of greater than about 150 MHz and up to about 300 MHz to produce relatively small heated focal zones with diameters smaller than 8 cm and as small as approximately 5 cm in relatively large tissue masses having cross sectional diameters greater than about 15 cm without excessively heating tissue surrounding the heated focal zone or creating hot spots in areas of the normal tissue away from the tissue to be treated. However, while the parent application considered heating of relatively small heated focal zones with diameters of 8 cm or less in relatively large tissue masses, it did not specifically address the issues of extremely small heated focal zones with diameters of less than about 3 cm which require higher frequency radio signals such as up to about 915 MHz. Tumors in the human brain or areas of other diseased tissue in the human brain are typically less than about 2 to 3 cm in diameter. Therefore, if hyperthermia is to be successfully applied to such areas of diseased tissue in the brain, the heated focal zone produced by the hyperthermia system should be able to produce heated focal zones of 3 cm or less.

Disease tissues of the brain are treated by phase array focusing of ultrasound energy which has been used to cause microbubbles that were injected into the brain to create a mechanical high pressure in an attempt to open the blood brain barrier. This is hoped to allow infused drugs to be able to pass through the blood brain barrier. Leinenga 2016 has reported using this approach with a scanning ultrasound system to remove amyloid plague and restore memory in Alzheimer's diseased mice. Invasive antennas have been used to radiate microwave energy to heat tumors of the brain. (Sneed). Zastrow has described a method to use phased array microwave heating to heat target regions of the brain to treat cancerous tissues of the brain by using a phase scanning method in an attempt to scatter unintended hot spots that occur in the brain by his methods while maintaining a primary heating focus in the target region of the brain. (Zastrow 2011, U.S. Pat. No. 9,079,011 B2 2015), This method of Zastrow fails to understand that there are certain critical design requirements needed for such a microwave array to prevent the occurrence of such secondary hot spots in the brain leading to the undesirable effort to time step scatter the unintended hot spots to various non-target regions in the brain. A study by Guerin 2017 numerically modeled the brain to evaluate the potential to heat sections of the brain with a theoretical phased array of 43,977 microwave dipole locations and 263,862 electric and magnetic point source (extremely small) dipoles. This showed the potential to create small focus fields in the brain, but the very large number of dipoles modeled is clearly impossible to actually implement. Also very small point source dipoles are extremely inefficient.

It has been observed in a large Finish study that Finish men who use a hot sauna at least 4 times per week over a long time period have reduced incidence of Alzheimer's Disease (AD), (Regular use of Sauna reduces Alzheimer's Disease as shown from a large Finish study: https://academic.oup.com/ageing/article-abstract/46/2/245/2654230/Sauna-bathing-is-inversely-associated-with). Another report is similar about the Finish study of regular sauna use from 2016: http://www.medscape.com/viewarticle/873851

There are commercial products by Virulite that have been developed to use infrared light array fashioned in a helmut configuration to expose the skin layers of the head to heating in an attempt to treat AD. (https://sciencebasedmedicine.org/science-by-press-release-a-helmet-to-fight-alzheimers-disease/, http://www.pat2pdf.org/patents/pat20120046716.pdf).

Another commercial product has been developed with a panel of IR lights to expose the skin in a heating application to treat AD conditions. (https://www.nirsauna.com.au/learning-centre/108-combination-heat-and-near-infrared-light-therapy-for-alzheimer-s-and-dementia, https://whsfzpq2.mykajabi.com/blog/reversing-alzheimer-s-and-parkinson-s-with-near-infra-red,) Animal studies have demonstrated that when mice which are old Alzheimer's disease conditioned mice have reversal of memory impairment and reduction of Amyloid deposits of the AD condition when exposed to microwave energy which is modulated similar to that of the global mobile communication system. (Arendash 4-2012). This implies exposure to such diseased tissues with AD may have beneficial memory by such treatment. It is known also that the hippocampus area of the brain is highly involved with memory and the formation of amyloid plague and other conditions that are related to the incidence of AD. (Cohen 1995, Flarmos 1991,) It has been shown that the stimulation of heat shock proteins (HSP) has provided a beneficial effect to reduce the amyloid plague formed in the brain with a beneficial effect of AD conditions. (Franklin 2005, Wang 2014, Smith 2005, Violet 2014, Ou 2014, see also the link: https://www.himdawi.com/journals/bmri/2014/435203/, also http://www.jneurosci.org/content/31/14/5225).

Salford in 2012 released a review study showing effects on the blood brain barrier by radiated electromagnetic fields both modulated and unmodulated for significant non-thermal levels of exposed power. Other studies related to the effects on blood brain barrier is Eberhardt 2009 which showed the effect of the BBB of rats exposed to cell phone signals. http://www.tandfonline.com/doi/abs/10.1080/15368370802344037.

The ability to focus microwave energy into deep locations in the brain can provide an improved therapy to treat brain cancerous tumors in combination with other standard treatments including radiation and chemotherapy. Sneed published in 1998 (article #2477) a randomized clinical trial showing focal heating of brain tumors when combined with radiation therapy provided improved clinical response for these patients compared to treatment with radiation alone. That study was done at the time when the radiation therapy was commonly performed with an invasive procedure called Brachytherapy where radiation sources were inserted into the tumor in the brain through plastic catheters. The use of these invasive catheters provided a means to insert microwave needle like antennas into the tumor for local heating of the tumor. However, since that time the radiation therapy practice has changed to a non-invasive approach so plastic catheters in the brain tumor to allow for insertion of the microwave antennas are no longer used. Thus, such tumor heating is not currently possible. The ability to non-invasively focus heating microwave energy into brain tumors could provide similar enhancement of the current non-invasive radiation therapy treatments as well as other heat treatments of diseased brain tissue not currently possible.

SUMMARY OF THE INVENTION

According to the present invention, an array of electromagnetic radiator applicators is utilized to surround the body of an adult size tissue mass and operated at a frequency range of 900 to 930 MHz, or greater, with a currently preferred frequency being about 915 MHz. The radiator applicators may be antennas of a dipole or equivalent radiator type. One preferred method is to have the antennas designed to radiate a linearly polarized electric field that is aligned with the body central axis. Such a configuration is described in U.S. Pat. Nos. 5,097,844 and 4,672,980. The space between the antennas and the body is filled with the customary bolus having a bolus media therein. The bolus media has a dielectric constant which is that of water at approximately 78. The use of the correct number of antennas and antenna spacing for a water bolus media is needed to avoid undesirable hot zones along the tissue surface that both would limit patient tolerance and also reduce the deep penetration capability. At a frequency of 915 MHz the wavelength in muscle tissue is 4.4 cm. If this was used on a tissue mass with a cross-sectional diameter of 15 cm to 18 cm, the diameter to wavelength ratio would be 3.4 to 4.1. For a tissue diameter of 15 cm the diameter to wavelength ratio would be 3.4 at 250 MHz. This frequency selection for adult body torso sizes is beyond that practiced in previous art. To provide the conditions of a phased array necessary to operate at such a high frequency, it has been found that there are critical applicator position and array sizes needed to avoid creation of high secondary hot spots in tissue away from the targeted tissues. The design of such an array requires a maximum spacing between antennas that are adjacent along a circumferential path (ring) around the tissue mass containing the tissue in need of treatment that is not more than 0.8 of the wavelength of the radio frequency signal at the operating frequency in the bolus media. Further, the maximum difference in phase at a bolus-tissue mass interface point between a radiated signal traveling through the bolus between the center of a radio frequency energy radiator applicator and the center of the tissue mass and a signal traveling through the bolus to that point from the center of an adjacent radio frequency energy radiator applicator should be no more than 135 degrees. This phase difference can be predetermined for the size of body tissue mass containing the tissue to be heated in relation to the size, shape; and positioning of the antennas of the array and the size of the bolus and the characteristics of the bolus media. When using a 3D focusing system such as described in U.S. Pat. No. 5,097,844 using three or more stacked antenna rings, the distance between adjacent stacked antennas (between adjacent antenna rings) should be no more than 0.8 of the wavelength of the radio frequency signal at the operating frequency in the bolus material, and the difference in phase at the bolus-tissue mass interface between signals from the center of aligned stacked radio frequency energy radiator applicators mid way between the rings is no more than 125 degrees. The dielectric of the bolus media also sets a limit to the position and spacing of the long axis stacked antennas for a particular frequency and tissue size.

The prior art has not considered the special limitations and constraints needed to implement a high frequency phased array that will be capable of producing a heated focal zone of volume and diameter not much larger than the typical deep tissue tumor to be treated and with adequate penetration depth to adequately heat such deep seated tissue. Improper selection of the applicator array design can result in less penetration depth, high superficial hotspots, degraded penetration when phase steering the heated focal zone, excess superficial fat heating, multiple hotspots, and an elongated shape in the deep energy and heated focal zone. These specific requirements have been discovered to be possible with a 915 MHz phased array of antennas that surround the body with common electric field polarization in typically 3 rings of antennas. Each of these three antenna rings typically contain between 16 and 24 antennas, with 24 antennas in each ring being preferred, resulting in a total of between 48 and 72 total antennas, with a total of 72 antennas being the preferred embodiment. It has been determined that with this number of antennas that the dielectric media between the antennas and the body surface can be water and comply with the specific design constraints provided herein. This design has been shown to provide a single dominant deep focus zone with minimal heating of other areas within the human brain and head. The application of this unique non-invasive focus capability provides the ability to selectively heat diseased or disease involved areas of the brain. The ability to provide selective heating within the human brain will increase bloodflow, oxygen, and other local tissue metabolic functions. Local heating in tissues has also been shown to increase the activation of heat shock proteins which are known to provide beneficial effects in these local tissues which include immune response activation. These effects are known to selectively enhance other cancerous tumor treatment methods such as radiation and chemotherapy. The activation of heat shock proteins has also been shown to improve symptoms related to Alzheiber's disease and dementia. As some animal studies have shown there can be different beneficial effects from continuous wave applied power or a modulated radio frequency or microwave EMF, the system configuration provides the function to provide either a continuous wave or modulated power. This can be provided by an electrically controlled attenuator which can be used to vary the amplitude of the radiated power. Published studies have shown benefits by such modulation that is similar to that of the Global Communications System for example.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1:
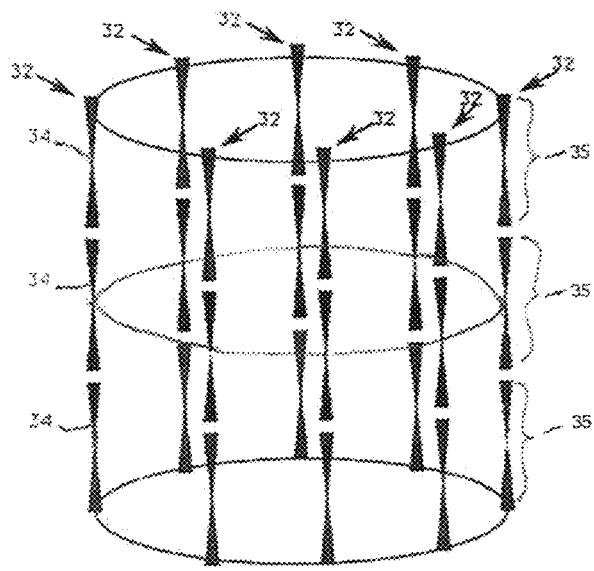
FIG. 1 is a view showing a cylindrical arrangement of groups of dipole antennas forming an electromagnetic applicator of the prior art 3-D hyperthermia system of U.S. Pat. No. 5,097,844.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENTS

The invention includes the recognition that at least four variables in a phased array radio frequency (RF) hyperthermia system are interdependent and critical to being able to produce a desired size of heating zone deep within a tissue mass containing a zone within the tissue mass to be heated to a desired minimum temperature while maintaining other tissue within the mass below such minimum temperature. The invention also includes specific arrangements of the parts of a phased array radio frequency hyperthermia system based upon the variables and interaction between the variables by which a small heating zone, such as the size of a typical tumor in the tissue mass, can be produced by such a system in the tissue mass. The current invention can produce an extremely small heating zone having a cross sectional diameter of about 3 cm or less which is about the typical size of a tumor within a human brain and other zones in the brain related to certain diseases of the brain. Since the variables and their interdependence are substantially the same as the variables found effective in the parent application, the discussion of the variables as provided in the parent application will be repeated here in connection with illustrations from the parent application. The parent application describes the invention to include specific arrangements of the parts of a phased array radio frequency hyperthermia system based upon the variables and interaction between the variables by which a relatively small heating zone, such as the size of a typical tumor, can be produced by such a system in a relatively large tissue mass such as represented by a human pelvis, abdomen, or thorax. As used in the parent application and herein in reference to the parent application, a relatively large tissue mass will be a three dimensional tissue mass having a cross sectional diameter of at least about 15 cm, which is larger than the head and neck area of most humans, but includes the pelvis, abdomen, and thorax of most humans which are usually between about 22 cm to about 33 cm. A relatively small heating zone will be a zone large enough to encompass a typical tumor occurring in a human pelvis, abdomen, or thorax, which will typically have a cross sectional diameter of about 8 cm or less, and small enough so that a substantial volume of normal tissue surrounding the tumor will not be heated to tissue damaging temperatures. A relatively small heating zone as described in the parent application will have a diameter of less than about 14 cm. The newly herein described and illustrated embodiments of the invention are designed specifically to create the heating zone, referred to as an extremely small heating zone, having a diameter of about 3 cm or less. However, phased array radio frequency hyperthermia systems for producing small heating zones of various other and in between sizes can be provided following the methods described in the parent application aided by the disclosure of the current application.

Figure 2:
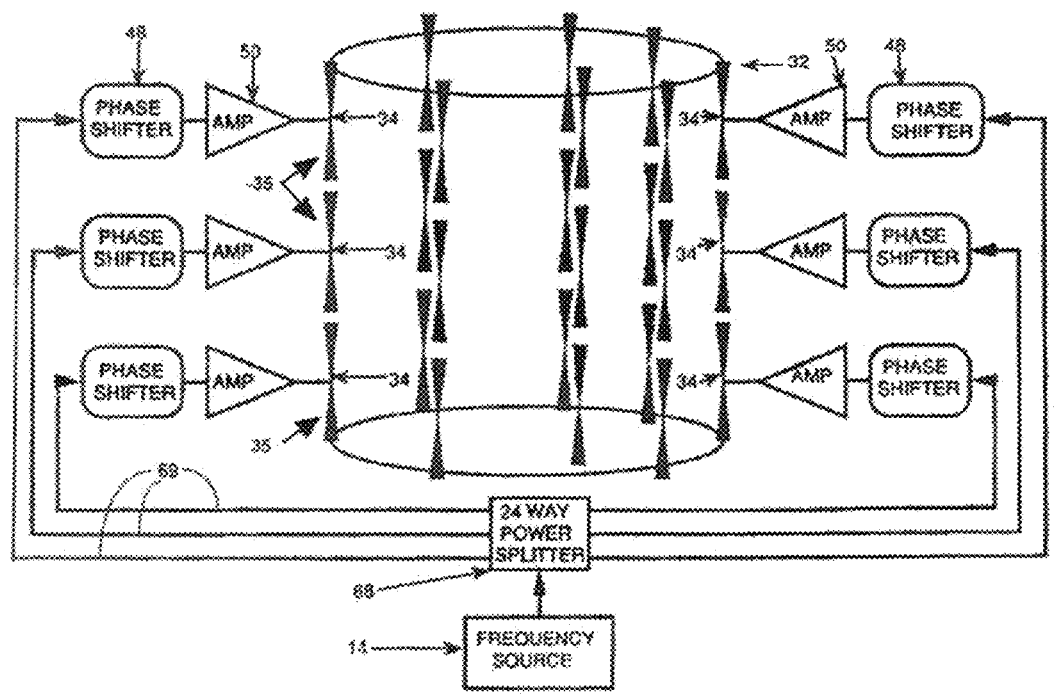
FIG. 2 is a schematic view showing in partial block form a prior art power connection arrangement for the dipole antennas of FIG. 1.

As indicated in the above State of the Art section, a phased array radio frequency hyperthermia system that allows for electronic steering and focusing of the heating pattern created by the system is shown and described in U.S. Pat. Nos. 5,097,844 and 4,672,980, both incorporated by reference herein in their entirety. The system as described in said U.S. Pat. No. 5,097,844 will be used as the illustrated example of an annular phased array radio frequency hyperthermia system for purposes of explaining the current invention. FIG. 1 herein is similar to FIG. 2 of said U.S. Pat. No. 5,097,844 and shows a 3-D cylindrical antenna array consisting of three rings 35 each including a plurality of, here shown as eight, applicators in the form of dipole antennas 34. The rings 35 are spaced or stacked side-by-side with the respective antennas 34 of each ring aligned end to end along the direction of the E-field polarization axis which is also the longitudinal axis of a tissue mass when placed inside of the rings. Each of the three end to end aligned antennas 34 is indicated as an antenna group 32. While various types of antennas can be used, FIGS. 1 and 2 show the antennas in the form of dipole antennas made of tapered metallic conductive strips with the RF power feed located midway between the two strips forming the dipole. The taper is increased outwardly from the central feed point to increase the frequency bandwidth and the near field energy along the region of the tips of the dipoles. The length of the dipoles should be determined in light of the operating frequency to prevent loss of energy. With each ring 35 having eight antennas 34, the three rings together have a total of twenty four antennas.

Figure 8:
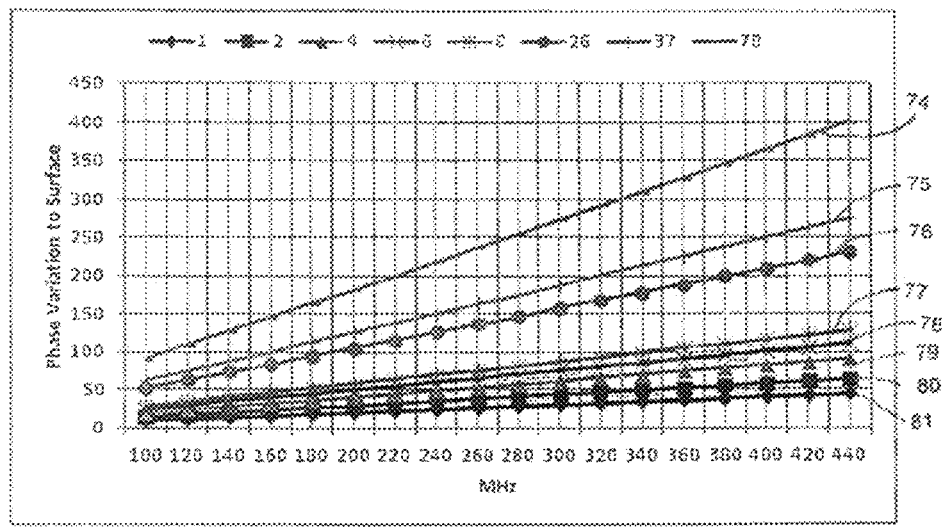

FIG. 2 herein is similar to FIG. 8 of said U.S. Pat. No. 5,097,844 and shows a twenty four amplifier system providing independent control of each antenna of the antenna array of FIG. 1. A twenty four way power splitter 68 is connected to a source of radio frequency power 14 of a particular selected frequency and provides a separate radio frequency power signal 69 for each of the twenty four dipole antennas shown in FIG. 1. While only six separate radio frequency power signals 69 from twenty four way power splitter 68 are shown in FIG. 2, and while, for clarity, FIG. 2 just shows the connection of the radio frequency signals 69 from the power splitter 68 connected to the three individual antennas 34 of two opposite antenna groups 32, there are twenty four such separate radio frequency power signals 69 transmitted from twenty four way power splitter 68. Each of the separate radio frequency power signals 69 is connected to a phase shifter 48. Each phase shifter 48 controls the phase of the power applied to an amplifier 50. Each amplifier 50 is connected to one of the twenty four dipole antennas 34 and provides the increase in signal power (gain) necessary for the particular dipole antenna 34 to which it is attached. While six of the connections described are shown in FIG. 2, similar connections are made for each of the antennas 34 in each of the antenna groups 32. It should be noted that since all twenty four radio frequency power signals 69 originate from a single signal power source 14, all twenty four radio frequency power signals 69 have exactly the same frequency.

Figure 3:
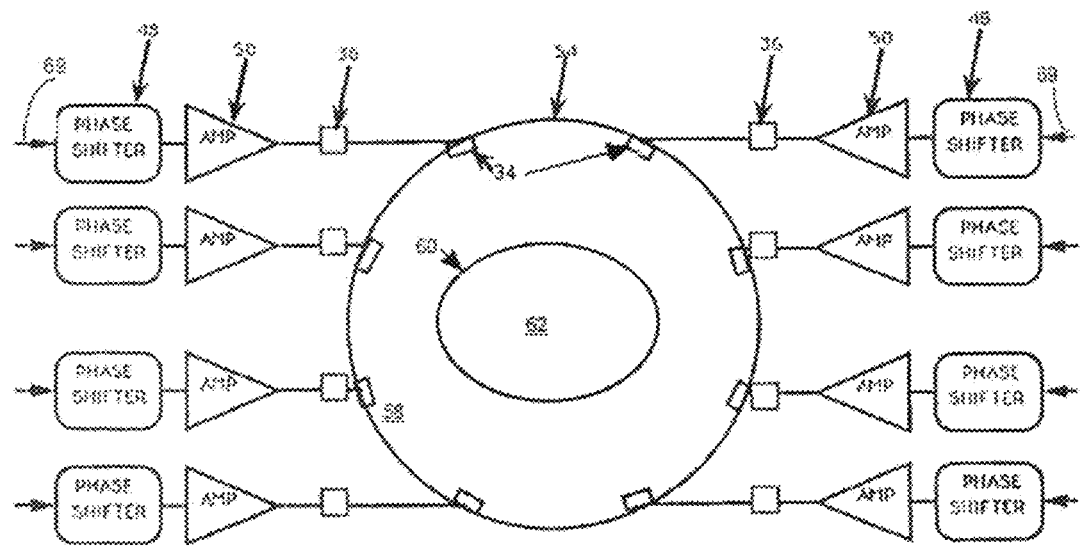
FIG. 3 is a partial schematic view showing in block form the power connection arrangement of FIG. 2 for one of the three stacked rings of the dipole antennas.
Figure 6:
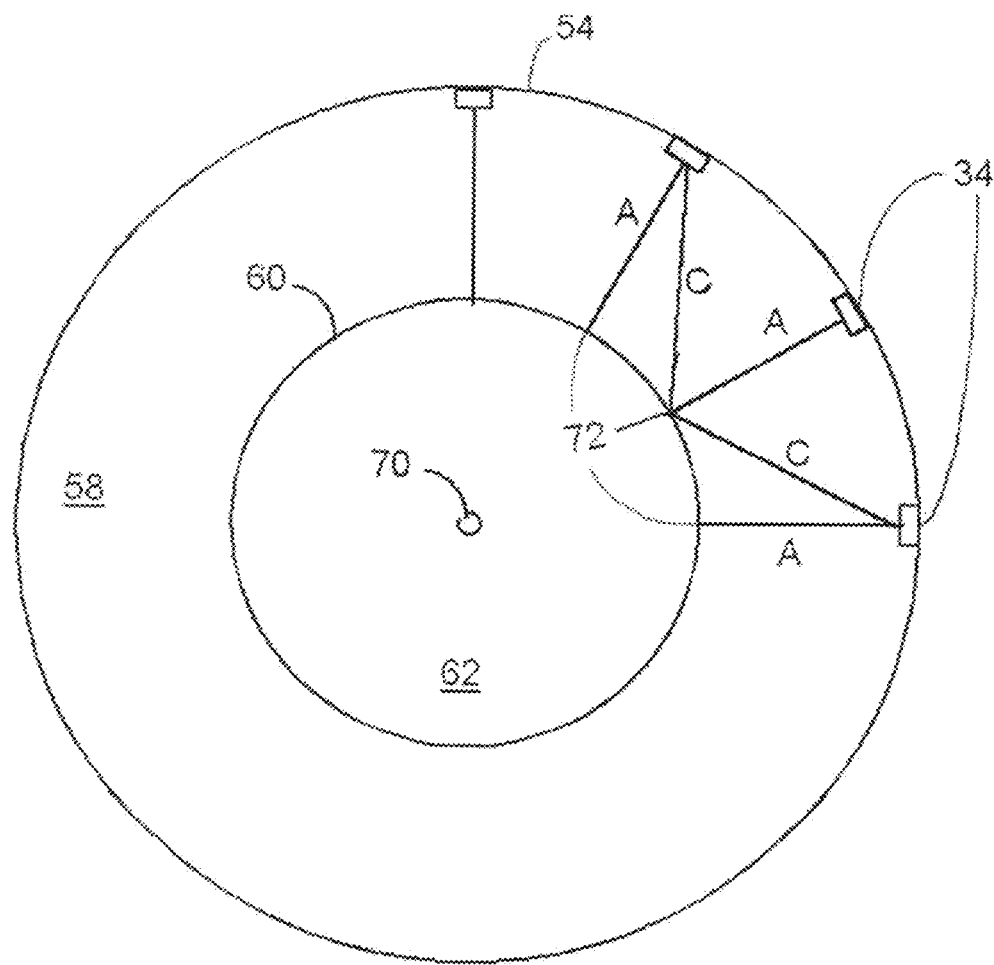
FIG. 6 is a horizontal section through an antenna ring and tissue mass centered therein showing selected signal paths from applicators through the bolus to the bolus—tissue surface interface.

FIG. 3 is similar to FIG. 6 of said U.S. Pat. No. 5,097,844 and shows the eight separate antennas 34 of one of the three stacked rings 35 of antennas shown in FIGS. 1 and 2. Each of the three rings 35 is similar. FIG. 3 shows the connections from the power splitter 68 to each of the eight antennas 34 in one of the three rings. Again, a separate radio frequency power signal 69 from the twenty four way power splitter 68 shown in FIG. 2 is connected to each of the eight phase shifters 48 shown in FIG. 3. Each phase shifter 48 controls the phase of the power applied to an amplifier 50. Each amplifier 50 is connected to one of the eight antennas 34 of the ring and provides the increase in signal power (gain) necessary for the particular dipole antenna 34 to which it is attached. With the arrangement shown in FIGS. 1-3, the phase and amplitude of the radio frequency signal to each of the dipole antennas 34 can be independently controlled to provide maximum flexibility in being able to control the steering and focus of the heated focal zone for the hyperthermia system.

Figure 4:
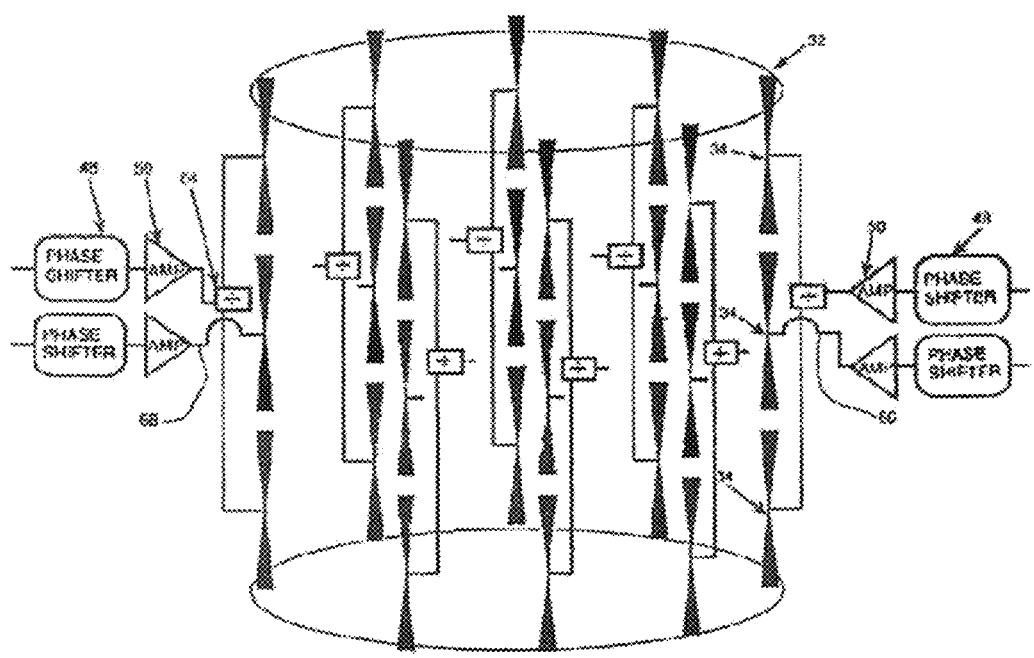
FIG. 4 is a partial schematic view similar to that of FIG. 2 showing in partial block form a different prior art power connection arrangement for the dipole antennas of FIG. 1.

While the hyperthermia system shown in FIGS. 1-3 as an illustrated example of a system usable for the present invention has independent phase and amplitude control of each antenna, the system can be arranged so that groups of antennas can be connected together to a single amplifier 50 so that the phase and amplitude for a group of antennas is controlled together. Examples of such arrangements are shown in U.S. Pat. No. 5,097,844. One such arrangement usable with the current invention is shown in FIG. 4. As shown in FIG. 4, the opposite end antennas 34 of each stacked group 32 of end to end antennas are connected through a splitter 64 to a common amplifier 50. Thus, each of these opposite end antennas of a group 32 receives a signal of the same or fixed relative phase and amplitude. When groups of antennas are connected together to a single amplifier 50, the number of separate radio frequency power signals required is reduced. Thus, for the system of FIG. 4, only a sixteen way power splitter is required rather than the twenty-four way power splitter shown in FIGS. 1-3. The capabilities of a system with groups of antennas connected to the same amplifier will generally be less that when each antenna is separately controllable as with the system of FIGS. 1-3. Also, with most arrangements used with the higher frequency signals of the system of the invention, separate control of at least twenty four separate antennas will be required.

As explained in U.S. Pat. No. 5,097,844, the dipole antennas 34 of the system may be formed along the inside wall of a clear plastic or dielectric cylinder 54 using well known adhesives or metal deposition processes. A thin patch of dielectric coating material can cover each of the antennas 34. A bolus 58 can be formed within the cylinder 54 by attaching a membrane 60 having ends sealed to the cylinder 54. A fluid input/output valve, not shown, can be mounted in the cylinder 54 for inflating the bolus with fluid, which fluid will also be referred to as the bolus media. The inflated bolus defines the body area in which the body (tissue mass) 62 containing the tissue to be heated is positioned, and provides an interface with the outer surface of the tissue mass. The bolus also provides surface tissue cooling, energy confinement, and improved antenna group coupling to the tissue of the body 62 in the body area. The fluid taught as used in the bolus in U.S. Pat. No. 5,097,844 is a high dielectric low loss fluid such as deionized water. U.S. Pat. No. 5,097,884 says that in practicing the invention it is important to take into account the dielectric characteristics of the bolus region and the body when planning the activation phase of the individual antennas 34. When using a bolus filled with deionized water, the deionized water has a dielectric constant very close to that of high water tissues such as muscle or tumor tissue. The use of deionized water improves the impedance match between the antennas 34 and the tissue in the body area 62. At the frequencies of interest, the impedance of the typical body tissue is approximately 44 ohms. The impedance of the antennas 34 and other electrical portions of the system is preferably 50 ohms in order to be compatible with standard components. The impedance of deionized water at the frequencies of interest is also approximately 44 ohms, so that all parts of the system are inherently closely matched.

The wavelength $\lambda$, of electromagnetic radiation propagating in a lossy medium, is given by the following expression $$\beta := \sqrt{2} \cdot \pi \cdot f \cdot \frac{\sqrt{\varepsilon r}}{c} \cdot \sqrt{\sqrt{1 + \left(\frac{sigef}{2 \cdot \pi \cdot f \cdot epso \cdot \varepsilon r}\right)^2} + 1}$$

$$\lambda := 2 \cdot \frac{\pi}{\beta}$$

Where f is the frequency in MHz, sigef is the media conductivity in S/m, $\varepsilon r$ is the relative permittivity of the media, epso is $8.854 \times 10^{-12}$ F/m, $\lambda$ is the wavelength in m, and c is the speed of light in vacuum, in m/s.

In proper operation of the phased array radio frequency hyperthermia system, the phase and amplitude of the radio frequency signals from each of the antennas need to be set so that the signals all arrive in phase at the desired heated focal zone location. This results in the signals constructively combining at this location. The phase of the signals radiated from the dipoles determines the location of the heated focal zone within the body. As dipoles have a wide pattern the heated focal zone is where the same phases exist in the superimposed beams. At the other points in the superimposed beams the phase is different and the energy partially cancels. In order to properly set the phase of the radio frequency signals radiated from respective antennas, the length of the signal paths between the respective antennas and the center of the desired heated focal zone need to be determined. Once the length of the signal paths is determined, the proper phase adjustments can be determined. The lengths of the signal paths can be approximated by representing the body 62, FIG. 5, having the desired heated focal zone therein, as a circular cylinder coaxial with the z-axis and having radius R from the z-axis to the outer surface of the body represented by bolus membrane 60. Let point P1 $(x_1, y_1, z_1)$ be the target point located within the body 62, and point P2 $(x_2, y_2, z_2)$ be the feed-point of the dipole antenna located on the dielectric cylinder 54 in the bolus space 58 outside of the body. The permittivity of the body and the bolus are given by $\varepsilon_1$ and $\varepsilon_2$, respectively.

Allowing for refraction, a ray propagating between P and P2 will pass through the outer surface of the body at point P3 $(x_3, y_3, z_3)$. By reciprocity, we consider the rays from P1 to P3 and from P3 to P2 to be given by the following vectors, where the parameter 0<t<1 through the transit:

$$\vec{S}_1^t = [x_1 + (x_3 - x_1)t]\hat{x} + [y_1 + (y_3 - y_1)t]\hat{y} + [z_1 + (z_3 - z_1)t]\hat{z} \quad (1)$$

$$\vec{S}_2^r = [x_3 + (x_2 - x_3)t]\hat{x} + [y_3 + (y_2 - y_3)t]\hat{y} + [z_3 + (z_2 - z_3)t]\hat{z} \quad (2)$$

The outward going normal to the cylinder at point P3 is given by $$\vec{N}^t = x_3 \hat{x} + y_3 \hat{y} \quad (3)$$

The corresponding unit vectors are given by $$\hat{s}_1 = \frac{(x_3 - x_1)\hat{x} + (y_3 - y_1)\hat{y} + (z_3 - z_1)\hat{z}}{\sqrt{(x_3 - x_1)^2 + (y_3 - y_1)^2 + (z_3 - z_1)^2}} \quad (4)$$

$$\hat{s}_2 = \frac{(x_2 - x_3)\hat{x} + (y_2 - y_3)\hat{y} + (z_2 - z_3)\hat{z}}{\sqrt{(x_2 - x_3)^2 + (y_2 - y_3)^2 + (z_2 - z_3)^2}} \quad (5)$$

$$\hat{n} = \frac{x_3 \hat{x} + y_3 \hat{y}}{\sqrt{x_3^2 + y_3^2}} \quad (6)$$

But the cosines of the angles of incidence and refraction are given by $$\hat{n} \cdot \hat{s}_1 = \cos(\theta_1) \quad (7)$$

$$\hat{n} \cdot \hat{s}_2 = \cos(\theta_2) \quad (8)$$

Thus, using Snell's law of refraction, we derive the following equation:

$$\sqrt{\varepsilon_1}\sqrt{1 - (\hat{n} \cdot \hat{s}_1)^2} - \sqrt{\varepsilon_2}\sqrt{1 - (\hat{n} \cdot \hat{s}_n)^2} = 0 \quad (9)$$

Equation (9) is solved iteratively with trial values of $x_3$, $y_3$, $z_3$ subject to the constraint that $$x_3^2 + y_3^2 + z_3^2 = R^2 \quad (10)$$

Then the calculated values of $x_3$, $y_3$, $z_3$ are used in Eq. (11) to determine the transit time T, so that the required phase lag may be determined.

$$T = \sqrt{\varepsilon_1 \mu_0}\sqrt{(x_3-x_1)^2+(y_3-y_1)^2+(z_3-z_1)^2} + \sqrt{\varepsilon_2}\sqrt{(x_2-x_3)^2+(y_2-y_3)^2+(z_2-z_3)^2} \quad (11)$$

Figure 5:
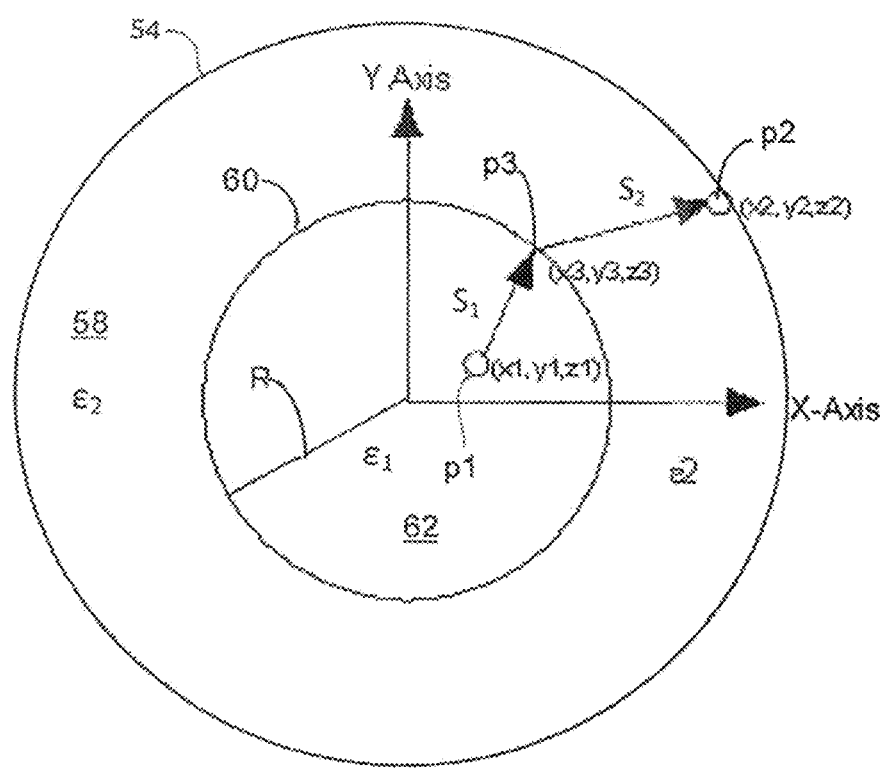
FIG. 5 is a horizontal section through an antenna ring and tissue mass centered therein showing a signal path from an applicator through the bolus and into the tissue mass to a focus zone therein.

It should be noted that the amount of refraction shown in FIGS. 5 and 6 is exaggerated for illustration purposes and generally will not be as great as shown. Further, when using a bolus filled with deionized water, the deionized water has a dielectric constant very close to that of high water tissues such as muscle or tumor tissue so there is very little refraction at the bolus-tissue interface, point P3.

The current state of the art is to select an operating frequency for the deep-heating phased array that has a wavelength long enough to avoid secondary standing waves within the tissue cross-section and that will provide deep penetration capability. For example, consider a circular cylinder having a diameter of 22 to 33 cm as a model to approximate the torso of an adult human. At a frequency of 100 MHz the wavelength in high water tissues such as muscle or tumor tissue is 29.3 cm. Thus, the ratio of the diameter of the torso tissue to the wavelength of the radio frequency signal in the tissue is 0.75 to 1.13 of a wavelength for the diameters of 22 and 33 cm, respectively. This avoids the potential for creating secondary standing waves that can create secondary heating peaks that would be away from the intended target tissue P1. However, at a frequency of 250 MHz the wavelength in high water tissues such as muscle or tumor tissue is 14.4 cm. If this higher frequency is used with a tissue diameter of between 22 and 33 cm, the ratio of the diameter of the torso tissue to the wavelength of the radio frequency signal in the tissue 1.53 to 2.3 of the wavelength. With this larger diameter tissue, creation of secondary heating peaks away from the intended target tissue is likely when using the shorter 250 MHz wavelength. This is why the commercial Sigma Eye phased array of the BSD-2000 system has a set maximum frequency of 100 MHz. While a high frequency of 434 MHz has been used in a radio frequency annular array hyperthermia system when the tissue portion of the body being treated is a neck portion of the body, the typical adult tissue diameter of the neck portion is about 12 cm. The wavelength in muscle tissue at 434 MHz is 8.8 cm. At 12 cm, the ratio of the diameter of the neck tissue to the wavelength of the radio frequency signal in the neck tissue is 1.37 of the wavelength. While close, this generally avoids the potential secondary heating peaks that would be away from the intended target tissue. However, if the 434 MHz frequency is used with a tissue diameter of between 22 and 33 cm, the ratio of the diameter of the tissue to the tissue wavelength is 2.5 to 3.75, respectively, of the shorter wavelength. With this larger diameter tissue, creation of secondary heating peaks away from the intended target tissue is likely when using the shorter 434 MHz wavelength. Adding more antennas and the number of RF control channels as well as a bolus dielectric lower than that of water and meeting the conditions of the current invention might reduce or eliminate the creation of the secondary heating peaks.

While U.S. Pat. No. 5,097,844 indicates that the normal frequency range for the system described in the patent for treating the torso portion of an adult is between about 50 to 1000 MHz and that it is most useful between about 60 to 220 MHz, as indicated above, the actual prior art systems are not operated above 120 MHz for heating tissue in the torso portion of the body. This is true even though U.S. Pat. No. 5,097,844 recognizes that these lower frequencies limit the precision to which the tissue can be selectively heated and that increasing the frequency would provide higher precision for the focusing. The diameter of the heated focal zone in the cylindrical plane is approximately between $\frac{1}{3}^{rd}$ to $\frac{1}{2}$ of a tissue wavelength. As previously indicated, most tumors in the torso portion of a human body are less than 8 cm. The need is that the heated focal zone should be able to penetrate to the center of the body of an adult torso and be capable of selectively heating targeted tissue to be heated that is approximately 8 cm in diameter or less. Selectively heating the targeted tissue means that the targeted tissue will be heated to the desired treatment temperature while the tissue surrounding the targeted tissue will not be heated to an extent that will damage such tissue. Thus, ideally, where the targeted tissue is about 8 cm in diameter, the heated focal zone produced by the annular phased array system will be about 8 cm in diameter without extending substantially beyond the 8 cm diameter. With such a system, this means that at all points within a sphere with a diameter of 8 cm, corresponding to a volume of 270 cubic centimeters of tissue, the relative SAR (Specific Absorption Rate, or absorbed power per unit mass) would be within 50% of the maximum SAR in the tissue within the sphere. The relative SAR for tissue outside of the sphere will be less than 50% of the maximum SAR in the tissue within the sphere. It is not necessary that the heated focal zone be completely confined to the tumor, but that there is greater localization or selectivity and less damaging heating of tissue outside of the diameter of the tumor or other diseased tissue to be treated than currently obtained in the current use of the radio frequency annular array hyperthermia systems with frequencies limited to 120 MHz. The smaller heating zone would minimize the excessive heating of normal tissues. If more selective deep heating is provided, it is expected that the target tissue could be heated to a higher temperature than is currently possible, thereby increasing the therapeutic benefit of the hyperthermia treatment without increasing toxicity to the body. At 250 MHz the wavelength in high water content tissue such as tumor or muscle is 14.4 cm so the focus diameter expected in the cylindrical plane would range from 4.8 to 7.2 cm. The expected long axis diameter of the central focus when optimized phase values are selected for the various antennas ranges from $\frac{1}{2}$ to $\frac{3}{4}^{th}$ of a tissue wavelength. For 250 MHz the 50% SAR expected long axis diameter (usually along the longitudinal axis of the tissue mass) would be from 7.2 to 10.8 cm, depending on the phase settings for optimal focusing.

The inventors have found that in order to increase the frequency used in an annular phased array radio frequency hyperthermia system to thereby reduce the size of the heated focal zone produced by the system within a relatively large tissue mass containing the tissue to be treated without creating undesirable hot spots in the normal tissue of the tissue mass away from the tissue to be treated and without creating undesirable hot zones along the tissue surface that would both limit patient tolerance to the treatment and reduce the deep penetration capability for such high frequency signals, a number of parameter adjustments not disclosed in U.S. Pat. No. 5,097,844 or other prior art, are required. These adjustments include the spacing between the antennas surrounding the body, which affect the number of antennas used, the size of the bolus, and the bolus media used in the bolus. All of these are interdependent and are dependent on the frequency used. These parameters and their interdependence will be described for use with an example frequency range between 200 MHz and 300 MHz used to produce a heated focal zone sized to treat a tumor or other tissue deposit having a major diameter of 8 cm or less located in an adult human torso, such as in a human pelvis, abdomen, or thorax. The example parameters are applied to the radio frequency annular array hyperthermia system as shown and described for FIGS. 1-3 with independent control of the phase and amplitude of the signal radiated by each antenna. It has been found that while the bolus media in the bolus needs to have a dielectric constant which is much greater than 1, as does the deionized water taught in U.S. Pat. No. 5,097,844 which has a dielectric constant of 78, that for use with the higher frequencies, the bolus media must have a dielectric constant which is lower than that of water which is 78. The lower dielectric constant media is necessary at these higher frequencies to minimize superficial hot spots and to also preserve a deep selective central focus with a practical number of antennas and control channels. The use of the correct bolus media is needed to also avoid undesirable hot zones along the tissue surface that both would limit patient tolerance and also reduce the deep penetration capability.

At a frequency of 250 MHz the wavelength in muscle is 14.4 cm. When used on tissue with a cross-sectional diameter of 22 cm to 33 cm the ratio of the tissue diameter to the tissue wavelength is 1.53 to 2.3. For a tissue diameter of 28 cm the diameter to wavelength ratio is 1.94 at 250 MHz. To provide the conditions of a phased array necessary to operate at such a high frequency the inventors have found that the array requires a maximum spacing between antennas that are adjacent along a ring that is not more than 0.8 of a wavelength in the bolus media. Further, the maximum difference in phase between adjacent antennas is 135 degrees at a common circumference point at the body surface (interface between the body surface and the bolus membrane) when the radio frequency signals are directed from the array applicators to the center of the tissue mass. This difference in phase can be predetermined for the size of body to be heated in relation to the size, shape, and positioning of the antennas of the array and the dielectric constant of the bolus media.

FIG. 6 is a representation of the cylinder 54 through one of the three stacked rings with eight antennas 34 evenly spaced around the inside of the cylinder 54 with a bolus 58 formed by membrane 60 attached at its ends to cylinder 54 to define a body area 62, shown here as cylindrical as in FIG. 5 for the cylindrical body used as a model for calculations rather than ellipsoidal as in FIG. 3, which is representative of the "Sigma Eye" configuration and is more representative of a human torso. The line 60 showing the membrane also represents the surface of the body surrounded by the bolus. The bolus 58 is filled with bolus media having a dielectric constant. In FIG. 6, the desired heated focal zone, which here is at the center of the body (the tissue mass having the tissue to be treated therein), the center of which is indicated as 70, is in the center of the array. The distance through the bolus from the center of an antenna 34 to the surface of the body 62 along a line from the antenna 34 to the center 70 of the body, indicated by points 72, is indicated by A. The distance through the bolus to a point 72 from the center of an adjacent antenna 34 is indicated by C. Examples of these distances when using eight antennas spaced evenly around the outer circumference of the bolus and having a 28 cm diameter body 62, are, for a 60 cm outer bolus diameter, A=16 cm and C=24 cm, for a 44 cm outer bolus diameter, A=8 cm and C=17 cm, and for a 36 cm outer diameter bolus, A=4 cm and C=14 cm. It has been found that the difference between the phases of the radio frequency signals at a point 72 on the surface of the tissue 62 directly from an antenna, distance A, and from an adjacent antenna, distance C, should be no more that 135 degrees. The wavelength of a particular frequency of signal in the bolus depends upon the dielectric value of the bolus, i.e., the dielectric value of the media filling the bolus.

Figure 7:
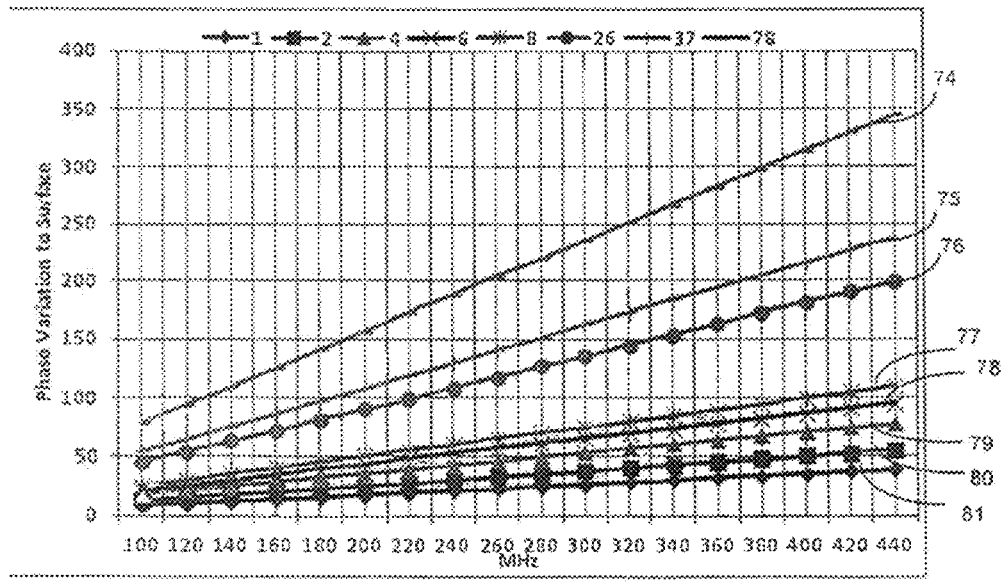
FIGS. 7-9 are graphs showing how the phase difference between the A and C distances shown in FIG. 6 changes with respect to frequency and dielectric constant and size of the bolus.
Figure 9:
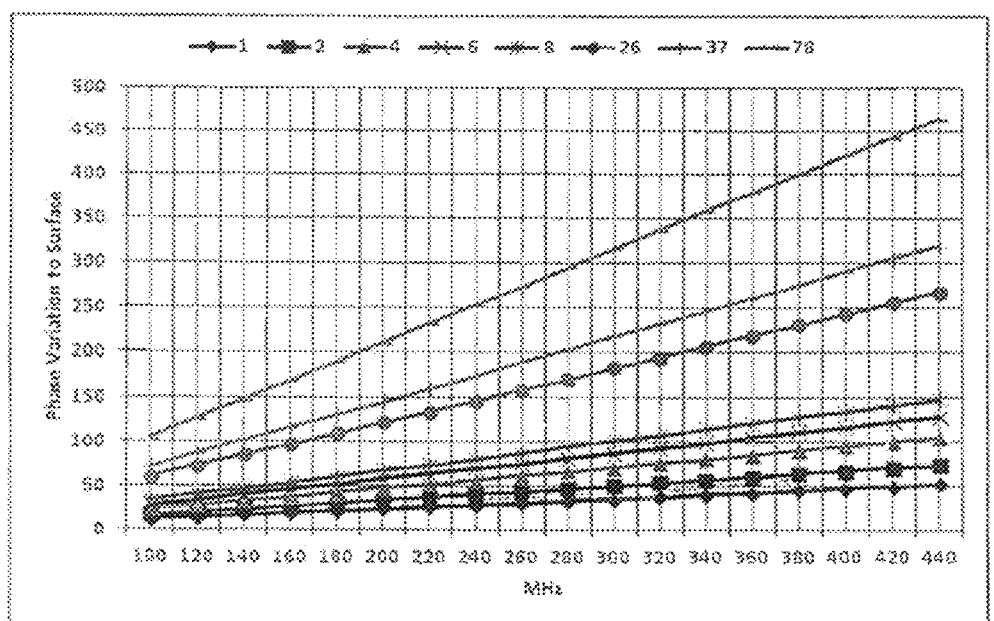

FIG. 7 is a graph showing how the phase difference between the A and C distances with respect to frequency and bolus media dielectric constant with the bolus having an outer diameter of 60 cm when signal path phase focusing is set on the radio frequency power channels. The vertical axis of the graph represents the phase difference at point 72 and the horizontal axis represents the frequency of the radio frequency signal from the antennas. Line 74 indicates the frequency difference with signal frequency when using a bolus media having a dielectric constant of 78. This is the value of dielectric constant of deionized water, the bolus media as used in the prior art. It can be seen that line 74 passes the phase difference of 135 at a signal frequency of about 160 MHz. Thus, when using a deionized water bolus of 60 cm outer diameter with a 28 cm body, the relationship determined by the inventors of having the difference in phase between distances A and C of less than 135 degrees is violated when using signal frequencies above about 160 MHz. Line 75 indicates the frequency difference when using a bolus media having a dielectric constant of 37. Ethylene glycol, which can be used as a bolus media has a dielectric constant of 37. When using a bolus media having a dielectric constant of 37, the signal frequency can be increased to about 230 MHz before the critical phase difference of 135 degrees is reached. Line 76 indicates the frequency difference when using a bolus media having a dielectric constant of 26. Propylene glycol, which also can be used as a bolus media, has a dielectric constant of 26. When using a bolus media having a dielectric constant of 26, the signal frequency can be increased to about 290 MHz before the critical phase difference of 135 degrees is reached. Line 77 indicates the frequency difference when using a bolus media having a dielectric constant of 8. Line 78 indicates the frequency difference when using a bolus media having a dielectric constant of 6. Line 79 indicates the frequency difference when using a bolus media having a dielectric constant of 4. Line 80 indicates the frequency difference when using a bolus media having a dielectric constant of 2. Line 81 indicates the frequency difference when using a bolus media having a dielectric constant of 1. It can be seen that by using a bolus media having a smaller dielectric constant than deionized water, such as ethylene glycol or propylene glycol, the frequency range for which the relationship of having the difference in phase between distances A and C of less than 135 degrees is extended. FIG. 8 is similar to FIG. 7 and shows the results when using a bolus having a smaller outside diameter of 44 cm. The graph line numbers between 74 and 81 are used in FIG. 8 to indicated dielectric constants of 78, 37, 26, 8, 6, 4, 2, and 1 respectively, similarly to FIG. 7. FIG. 9 is a similar plot showing the results when using a bolus having a still smaller outer diameter of 36 cm. FIGS. 7-9 show that for a particular bolus dielectric constant, as the bolus diameter gets smaller, the signal frequency maximum to meet the requirement of having the difference in phase between distances A and C of less than 135 degrees increases.

Figure 10:
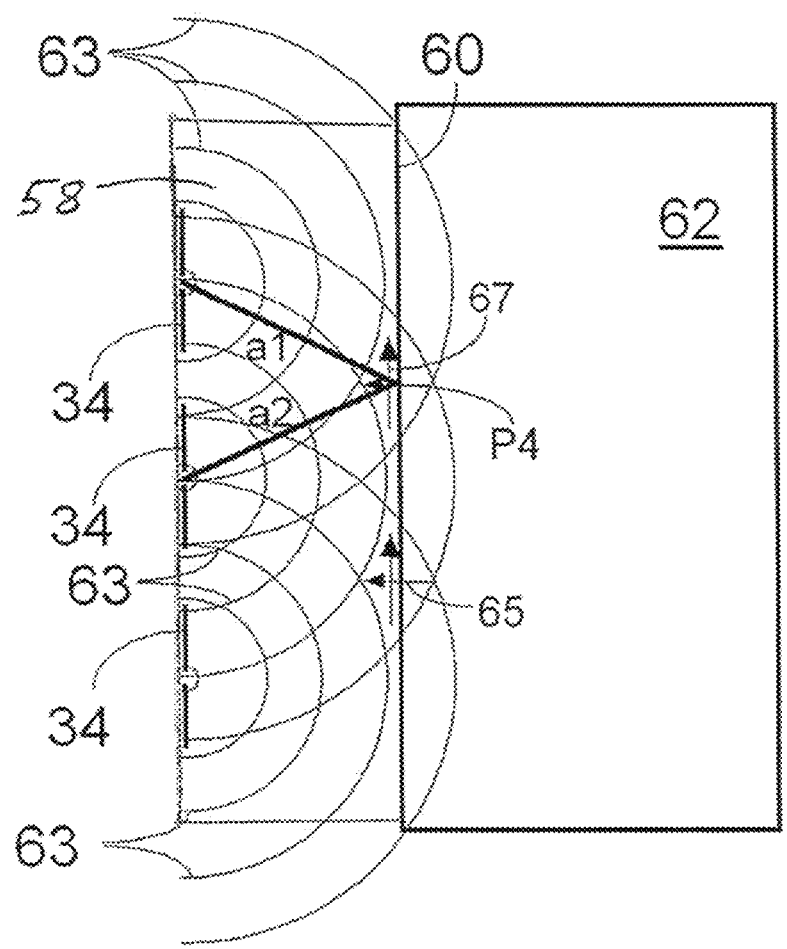
FIG. 10 represents the radio frequency signals radiated from the applicators stacked along the longitudinal axis of the tissue mass.

FIG. 10 represents a group 32 of the three stacked antennas 34 as shown in FIGS. 1-4, positioned along and spaced from the side surface, indicated as 60, of a tissue mass such as shown by 62 in FIG. 3 as representing a human torso containing the tissue to be heat treated therein. Such tissue mass will generally have an outer surface fat tissue layer surrounding the muscle tissue therein. The antennas 34 are located in a bolus 58, with the space between the antennas 34 and the tissue surface 60 being the bolus 58 as shown in FIG. 3. During operation of the system, each of the antennas 34 will radiate radio frequency signals, indicated as 63, of a particular frequency and phase toward the tissue mass 62. These signals will be superimposed along the surface 60 of the tissue and cause a horizontal electric field that is perpendicular to the tissue surface at the common point of intersection to the tissue surface fat layer. The horizontal electric field is indicated by arrow 65. The dominant direction of the electric field produced by the antennas is indicated by arrow 67. Surface fat tissue heating is strongly increased by such perpendicular electric fields. FIG. 10 shows equal length signal paths a1 from an end, dipole antenna 34 and a2 from a central dipole antenna 34 which intersect at a point P4 along the tissue surface midway between the two antennas from which they emanate. As indicated, these signals will be superimposed at point P4 and cause a horizontal electric field indicated by arrow 65 that is perpendicular to the tissue surface at point P4. When the electric field radiated from these two antennas are at the same phase, there is a cancelation of the perpendicular field at this intersecting signal path location, P4, which will reduce heating of the fat tissue at that point. If however, the radiating phase of these two antennas is different, then the superimposition of the two signals forming the perpendicular electric field do not cancel but their respective powers will add to create a perpendicular electric field value which will cause fat tissue heating. If, for example, the radiating phase from the respective antennas for signal paths a1 and a2 is different by 90 degrees, such a phase setting will cause the radial E field 65 that is perpendicular to the tissue surface at point P4 to be at a 90 degree phase angle. Such a field may cause excessive fat heating. More than a 90 degrees difference is even worse for fat heating. Further as the phase difference exceeds 125 degrees, it becomes likely that there will be multiple central foci formed which is especially likely at the higher frequencies described such as 434 MHz. This is most critical and evident if the three phases are 180 degrees different in these longitudinal axis stacked dipoles, because there would clearly be an energy focus offset to the longitudinal axis on each side of the primary central focus. Therefore, in a stacked phased array design in a radio frequency annular phased antenna array hyperthermia system, two limitations should be met. In such a system the respective stacked antennas should not be spaced apart along the longitudinal axis of the tissue mass a distance that would result in a 3D focus phase difference that is more than 125 degrees. Also the actual separation distance of the longitudinal stacked antenna feed points should not exceed a distance that is more than a distance representing a 0.8 of the bolus media wavelength at the operating frequency of the system. This will avoid excessive heating displaced along the longitudinal axis from the primary focus center (desired heating zone). Also, the respective stacked antennas should not be located and operated so that the phase difference between signals from adjacent antennas at the point of intersection of equal length paths from the adjacent stacked antennas with the tissue surface, point P4, are greater than 125 degrees. This will moderate the potential for superficial fat tissue heating from the resulting radial E-fields at the bolus fat tissue interface. Note that the design of an antenna array spacing and operating frequency and bolus all relate to the needed phase between adjacent antennas to achieve the central focus as determined by signal path calculations.

The dielectric constant of the bolus media also sets a limit to the position and spacing of the long axis stacked antennas, i.e., the spacing between antenna rings, for a particular frequency and tissue size.

Figure 11:
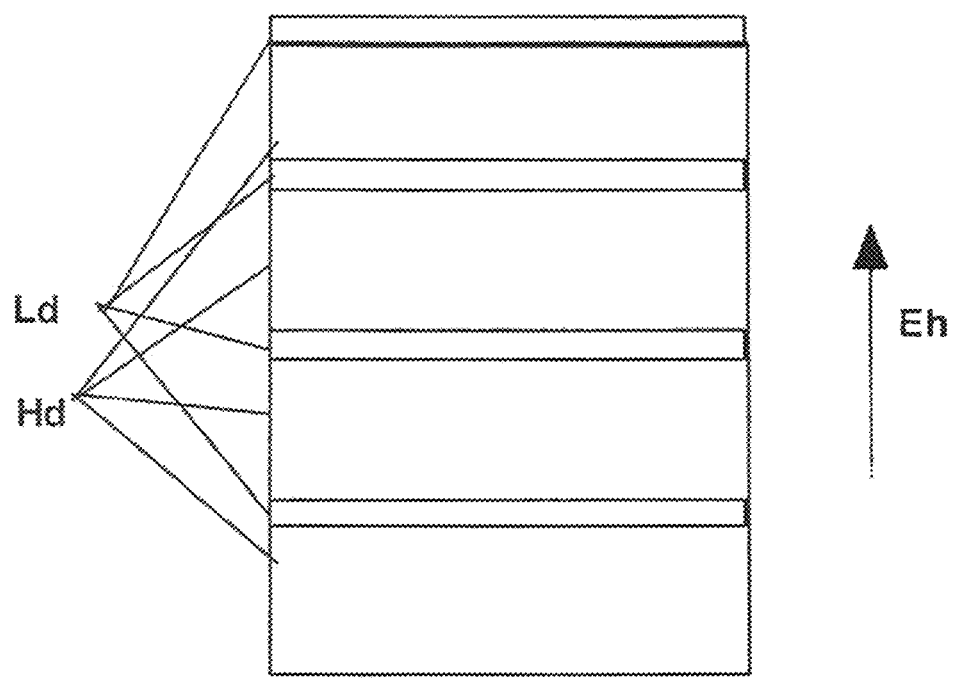
FIG. 11 shows an artificial dielectric that can be used with the invention.

As indicated above, the bolus media used can be critical in meeting the requirements set forth in this invention. The dielectric constant of the bolus media will determine the wavelength of a signal in the bolus media. If a bolus media having the desired dielectric constant and desired other properties is not available, an artificial dielectric media may be able to be constructed with a combination of high and low dielectric constant materials, such as with deionized water and plastic. FIG. 11 shows how an artificial dielectric can be made for radiating fields that are linear using high and low dielectric plate sections. The layered dielectrics of a low and high dielectric material can cause an effective artificial dielectric that has an effective dielectric constant between the dielectric constants of the two layered dielectrics. Such dielectric interface surfaces are to be primarily perpendicular to the dominant electric field.

When the electric field is dominantly perpendicular to dielectric plates of different dielectrics, the effective dielectric constant can be made to be a value between the dielectric constants of the two dielectrics. For the construction shown in FIG. 11, Ld is a plate or vane of low dielectric constant material, such as plastic or rubber, and Hd is a plate or vane of high dielectric constant material. Eh is the dominant electric field that is perpendicular to these plates or vanes. To apply this, the distance between the plates of the same kind must be less than a quarter of a wavelength of the media between the plates. The dielectric constant is determined by the equation:

$$e3 := \left[ \frac{e2 \cdot (t2 + t1)}{\left(e2 \cdot \frac{t1}{e1}\right) + t2} \right]$$

Where e1 is the Ld dielectric, e2 is the Hd dielectric, t1 is the Ld thickness, t2 is the Hd thickness and e3 is the resultant equivalent dielectric of the combined media.

Rather than the LD or HD being a plate or vane of material, either could be a dielectric material receiving space or receiving chamber. For example, the HD in FIG. 11 could be a space between LD plates which receives a high dielectric constant material, such as deionized water, or a chamber which receives the deionized water. The LD material could be a plastic or rubber chamber filled or partially filled with air or with a low dielectric constant material. A bolus could be constructed for use between the applicators and the body tissue to be treated where the low dielectric constant material is flexible plastic or rubber sheet material secured in the bolus and having space between each sheet to hold deionized water as the high dielectric constant material. The plastic or rubber sheet material can also form chambers which can be filled with either high dielectric constant material or low dielectric constant material.

While dipole antennas have been described for the applicators in the illustrated embodiments described above, various other types of antennas can be used such as slot antennas, patch antennas, or any other standard radio frequency or microwave antenna. In addition, while antennas that dominantly provide a linear polarized electric field that is dominantly aligned with the central body axis will be used, other alignments and polarizations can be used. For example, various rotated antenna alignments as well as orthogonal antenna pairs can be used to provide for bending of the electric fields in the body target areas that might be useful for overcoming a shadowing effect that may occur from different dielectric structures such as deep bone, fat, or air regions near the target zone.

Figure 12:
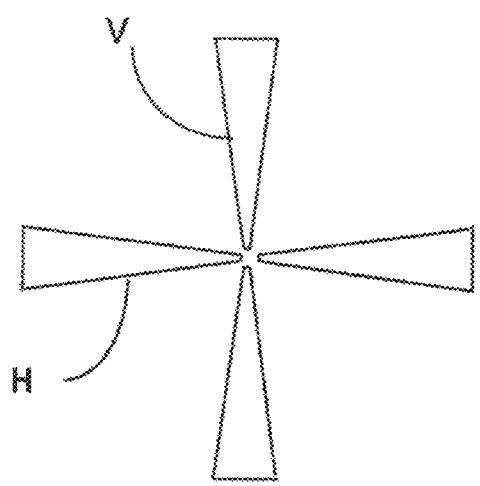
FIG. 12 shows an orthogonal dipole antenna pair usable with the invention.

FIG. 12 shows an orthogonal dipole antenna pair usable with the invention. This antenna includes two separate dipole antennas formed together as a pair. The dipole V radiates a dominant electric field polarization that is in the Z axis. The H dipole radiates a dominant electric field polarization that is in the X axis. Each dipole can be connected to a separate amplifier channel with its own power and phase control but operating at the same frequency. If there is no power on the dipole H the electric field is dominantly aligned along the Z axis in the dipole central zone as it radiates from the dipole. If there is no power on the dipole V the electric field is dominantly aligned along the X axis in the dipole central zone as it radiates from the dipole. If there is equal power on the dipoles V and H and the phase of V is the same as that of H, the radiated electric field is dominantly linear and aligned at a 45 degree angle to the X and Z axes. Each dipole can have a different relative phase to the other dipole. As the relative phases are changed and the relative power to each are changed, the polarization can change from various linear polarized angles to elliptical or circular polarization.

Figure 13:
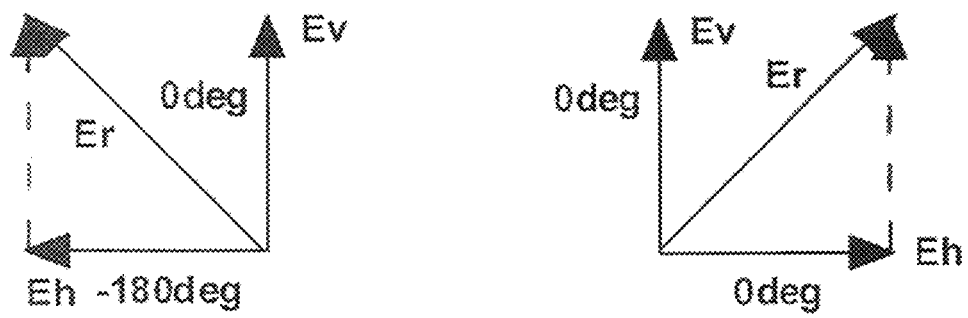
FIG. 13 shows how the electric field in the vertical and horizontal axis can be altered in the relative phase to change the resulting electric field.

FIG. 13 shows how the electric field in the vertical and horizontal axis can be altered in the relative phase to change the resulting electric field to be tilted by + or −45 degrees using either a 0 or 180 phase difference.

Er shows how linear electric field polarization can be radiated by changing the relative phase between the two orthogonal dipoles. If there is equal power on the dipoles V and H and the phase of V is 90 degrees different than that of H, the radiated electric field is dominantly circularly polarized. Circularly polarization is when the pointing direction of the radiating electric field rotates in the plane that is perpendicular to the radiating direction as it travels away from the source. The relative phase between the H and V dipoles can change from right hand to left hand circular polarization as well as creating elliptical polarization radiated fields.

The phased array of such orthogonal dipole pairs can results in significant differences in the tissue heating pattern generated. The ability to rotate the polarization angle can also alter the electric fields between various tissues of the body. This can be used to improve heating in areas that may be otherwise heated less. An example of this is the rectal area that is below the bending spinal bone area of the pelvis that is known to have a zone less heated adjacent to the bone due to the dominance of a perpendicular electric field at the tissue to bone interface.

Figure 14:
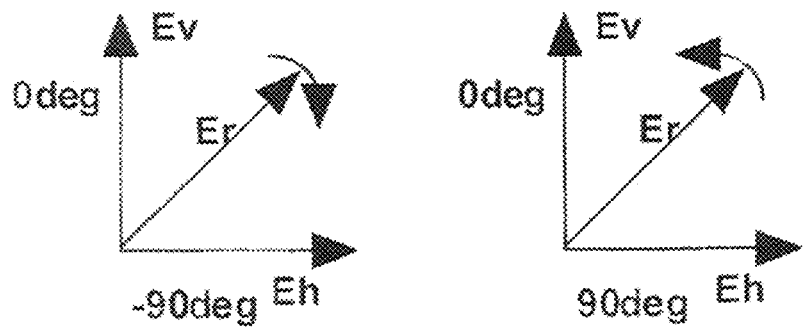
FIG. 14 shows how a change in relative phase of + or −90 degrees can cause a right hand or left hand circularly polarized radiated electric field

FIG. 14 shows how a change in relative phase of + or −90 degrees can cause a right hand or left hand circularly polarized radiated electric field. Er shows how circularly polarized electric fields can be radiated by changing the relative phase between the two orthogonal dipoles. When this capability is part of a phased array system, it provides additional and unique capability to control the heating fields to better heat tissues of the body. This is particularly the case if there is some tissue target zones that may be heated less due to the dominant electric field polarization in relation to neighboring tissues that are of a different dielectric.

It has been found by the current inventors that the special design considerations and limitations for an annular phased array hyperthermia system as set forth above can also be applied to construct and operate an annular phased array hyperthermia system that uses radio frequency signals of frequency between about 900 to about 930 MHz, preferably about 915 MHz, which surrounds the head of a patient and can produce an extremely small heated focal zone in the brain of the patient having across sectional diameter of about 3 cm or less. When using three rings of antennas as in the previously illustrated embodiments and using deionized water as the bolus media (dielectric constant of 78), it has been found that such an annular phased array hyperthermia system can be constructed using between 16 and 24 antennas in each ring, with 24 antennas in each ring being preferred, resulting in a total of between 48 and 72 total antennas. These can be arranged and controlled to provide selective heating within the human brain to provide hyperthermia to tumors or other diseased tissues within the brain, such as within the hippocampus of the brain, and to increase blood-flow, oxygen, and other local tissue metabolic functions.

Figure 15:
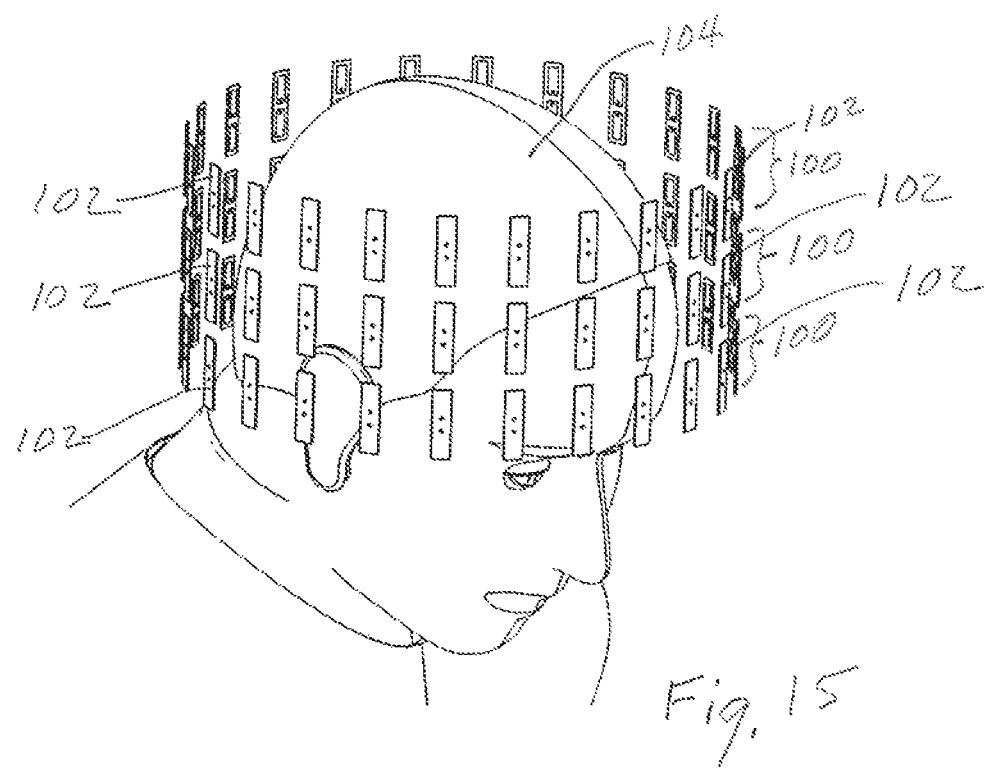
FIG. 15 is a schematic view of three rings of antennas encircling a head of a patient.
Figure 16:
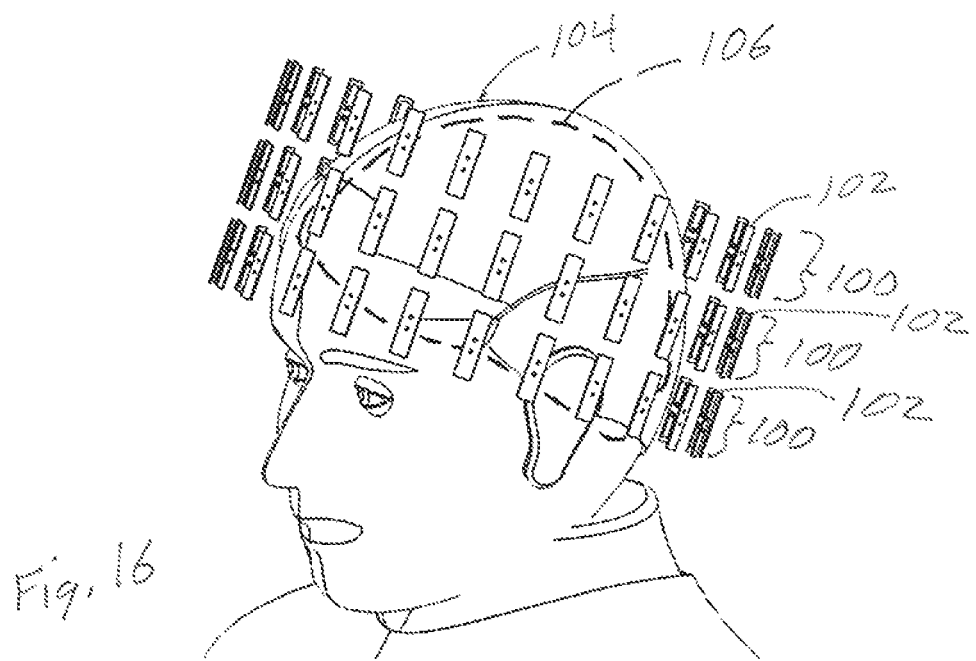
FIG. 16 is similar schematic view from the opposite side of the head showing a brain within the head to thereby show the arrangement of the antennas with respect to the brain within the head.
Figure 17:
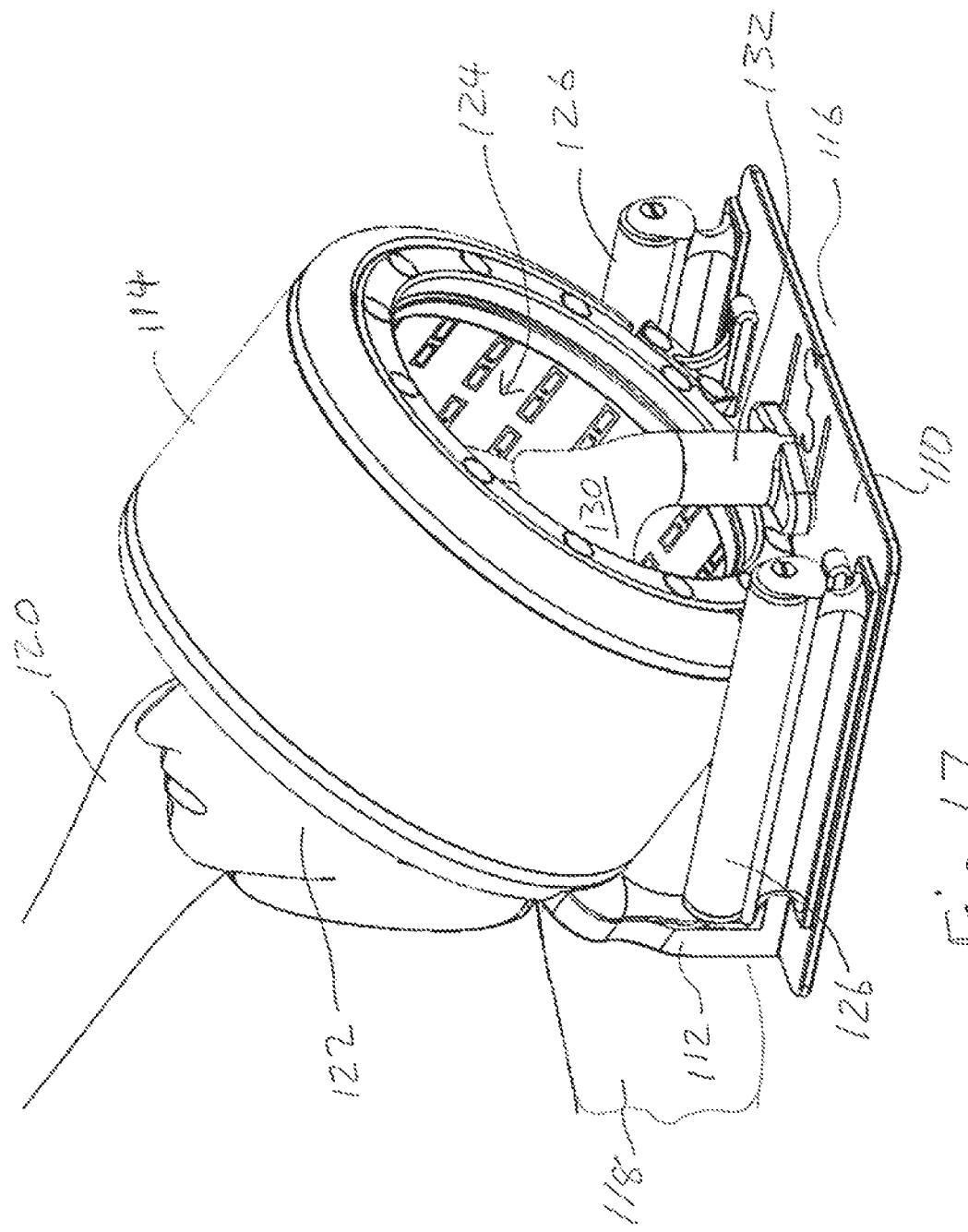
FIG. 17 is a pictorial view of the back of an applicator of the invention showing the head of a patient in the applicator.
Figure 18:
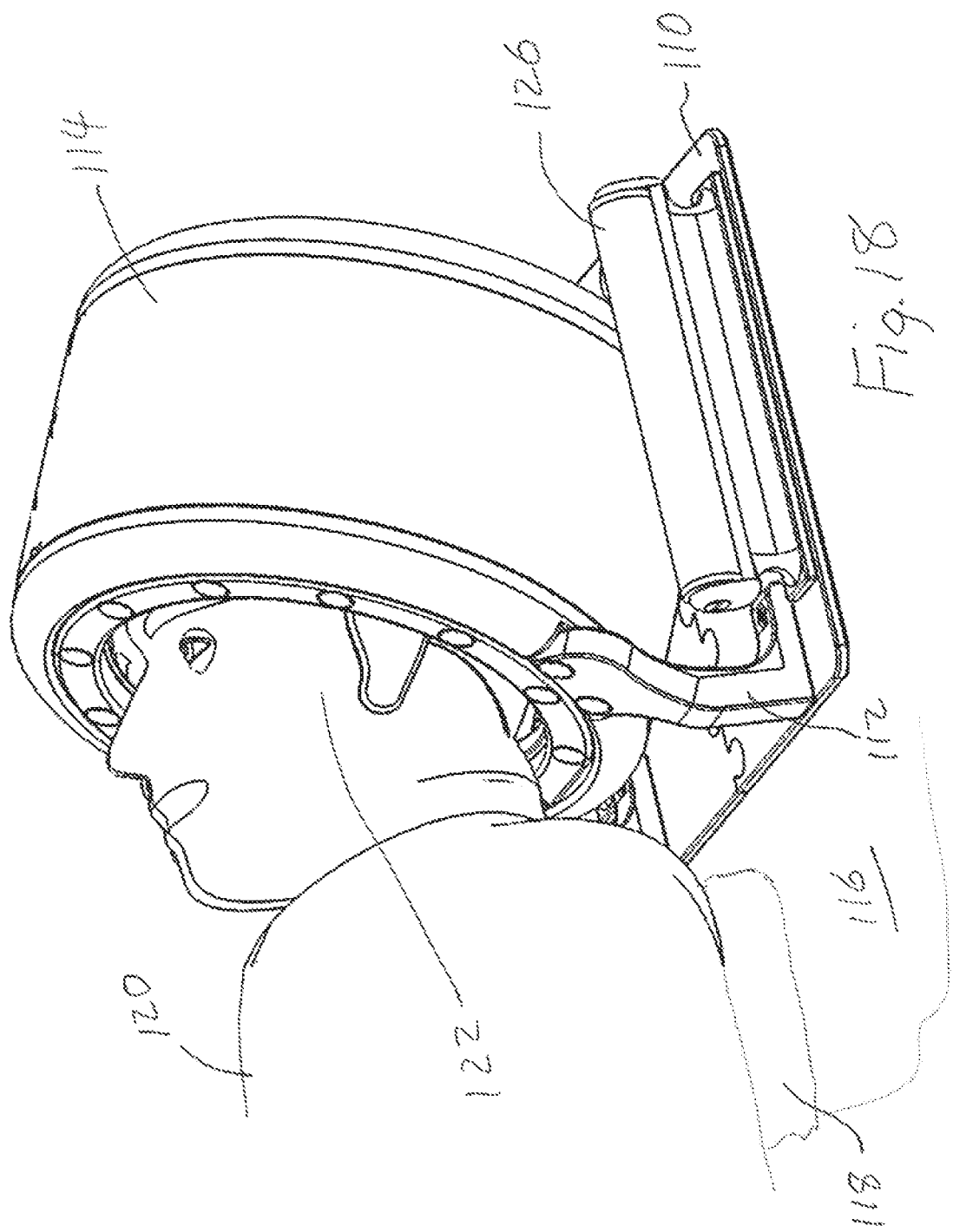
FIG. 18 is a pictorial view of the front of the applicator of FIG. 17.
Figure 19:
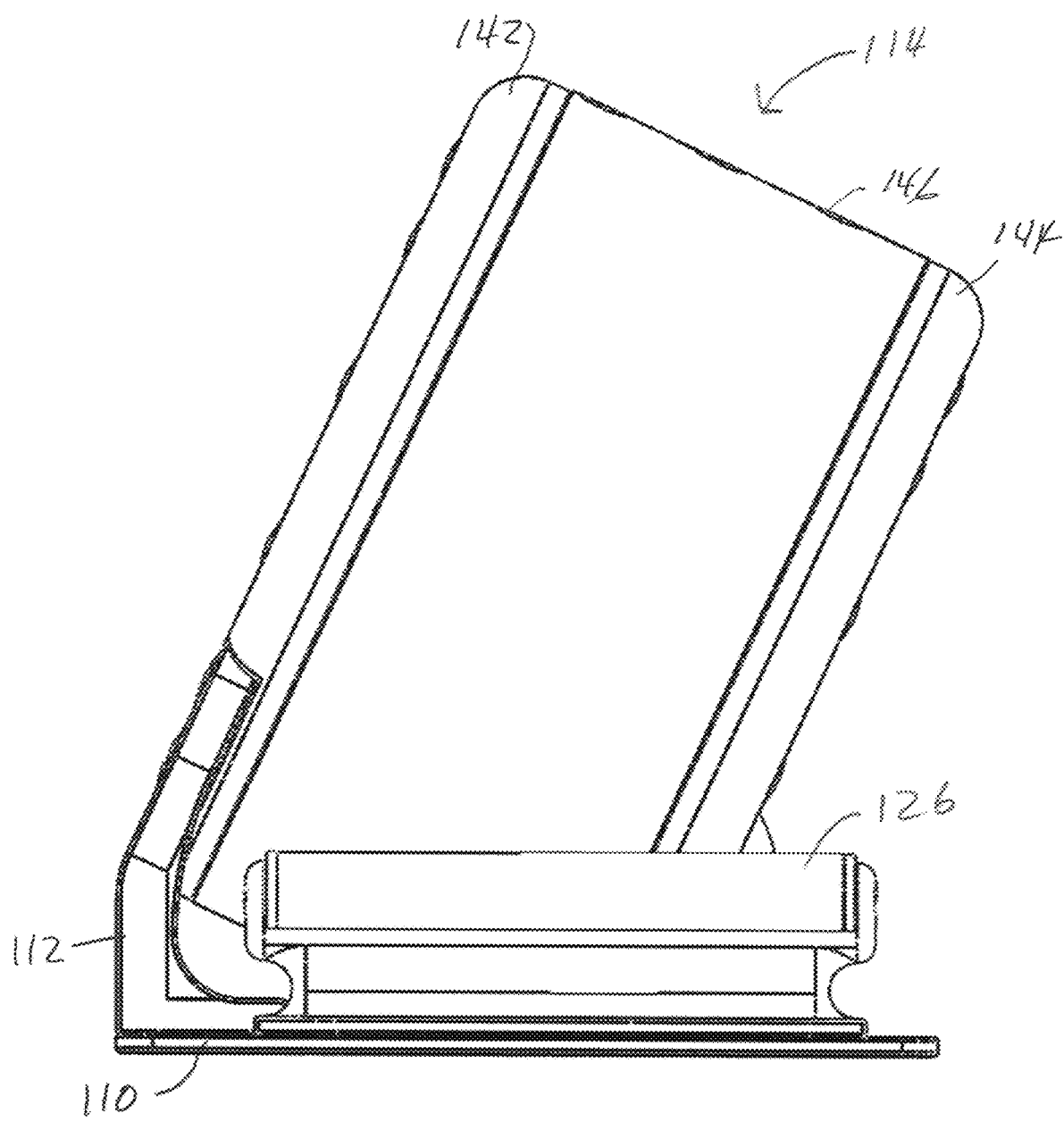
FIG. 19 is a side elevation of an applicator of the invention as shown in FIG. 17.
Figure 20:
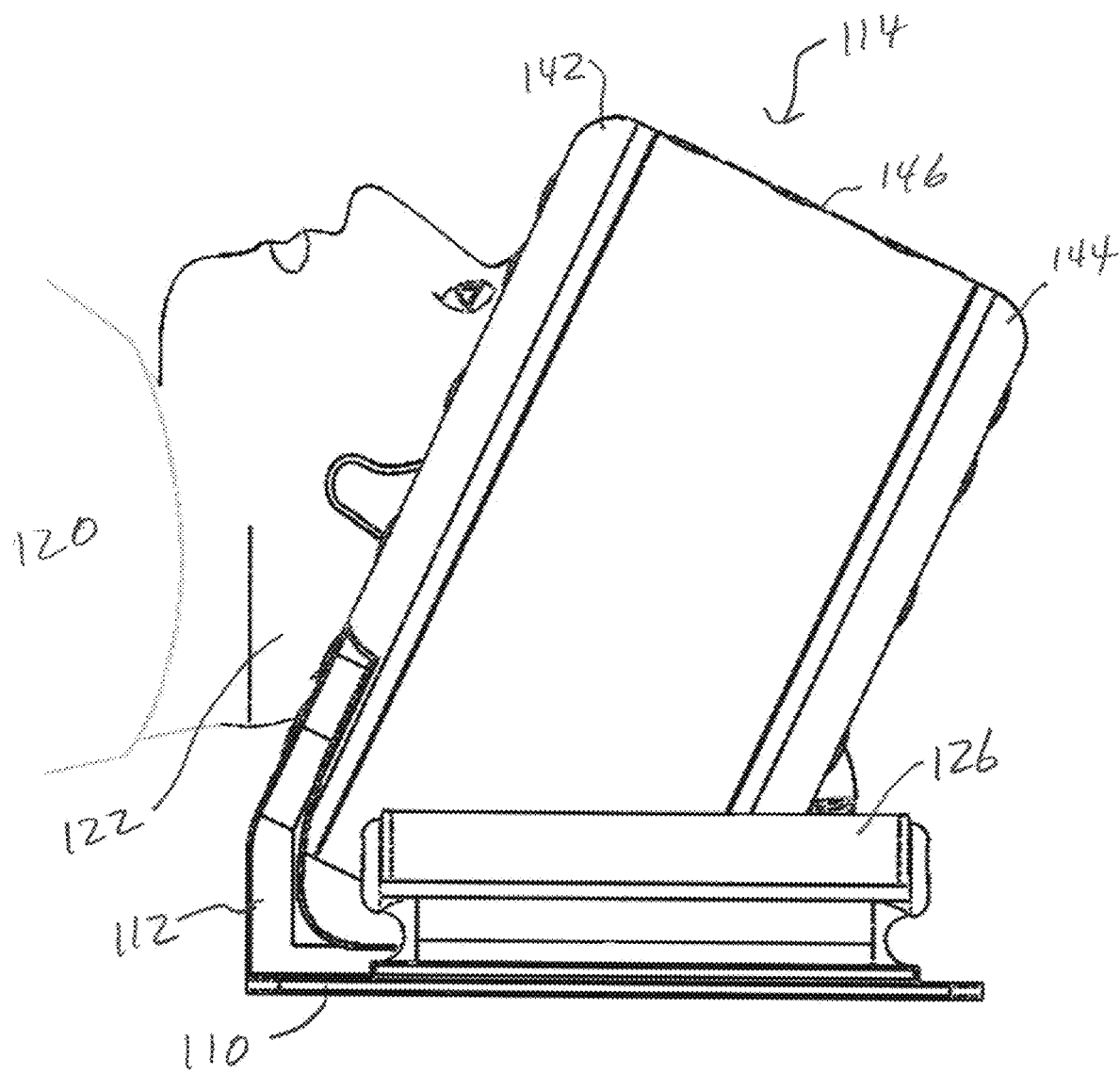
FIG. 20 is a side elevation of the applicator of the invention as shown in FIG. 19 and showing a patient's head in the applicator.

FIG. 15 is a schematic view of three rings 100 of antennas 102, here shown as dipole antennas, encircling ahead 104 of a patient. FIG. 16 is similar schematic view from the opposite side of the head showing a brain 106 within the head to thereby show the arrangement of the antennas with respect to the brain within the head. Each illustrated ring of antennas includes 24 individual antennas 102.

FIGS. 17-25, illustrate an embodiment of an annular phased array hyperthermia system applicator structure for receiving and holding the head of a patient to be treated and positioning three rings of antennas around the head of the patient. As shown, the applicator structure includes a base 110 with brackets 112 extending upwardly from base 110 to attach antenna support housing 114 to base 110. In the illustrated embodiment, base 110 is adapted to rest on a flat patient support surface 116 which supports a patient support pad or mattress 118 upon which a patient 120 lies to position the patient's head 122 for insertion into an opening 124 of antenna support housing 114. Silicone gel tubes 126 are mounted on opposite sides of base 110. These are used to correct imaging for the drift of the magnetic field over the course of treatment when magnetic resonance imaging is used for temperature sensing and control during hyperthermia treatment. Base 110 may include resilient material such as a plastic or rubber pad on it bottom surface to help hold it in place on the patient supporting surface 116 and so it does not scratch the patient supporting surface 116.

Figure 21:
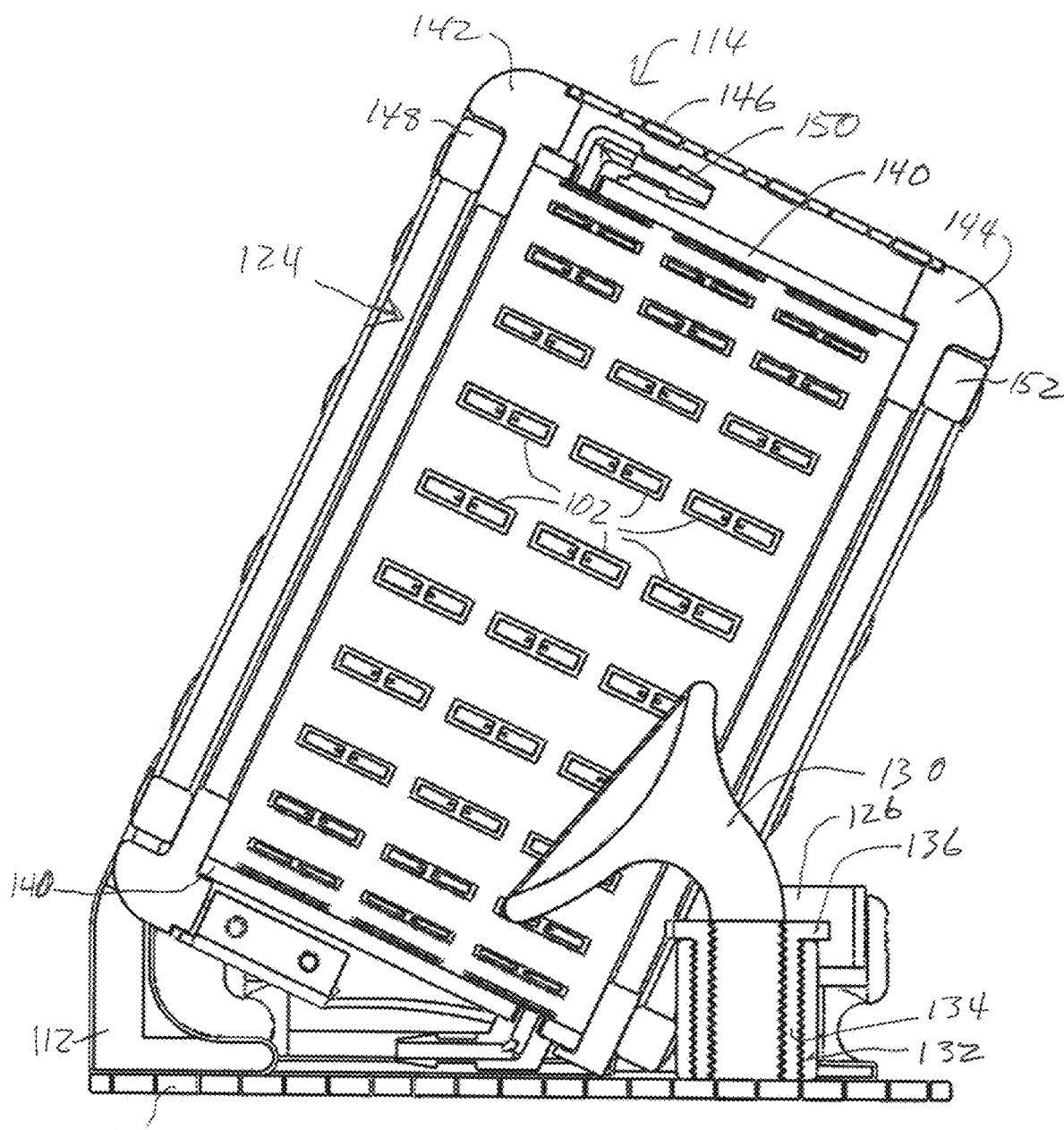
FIG. 21 is a vertical section of the applicator as shown in FIG. 19.
Figure 22:
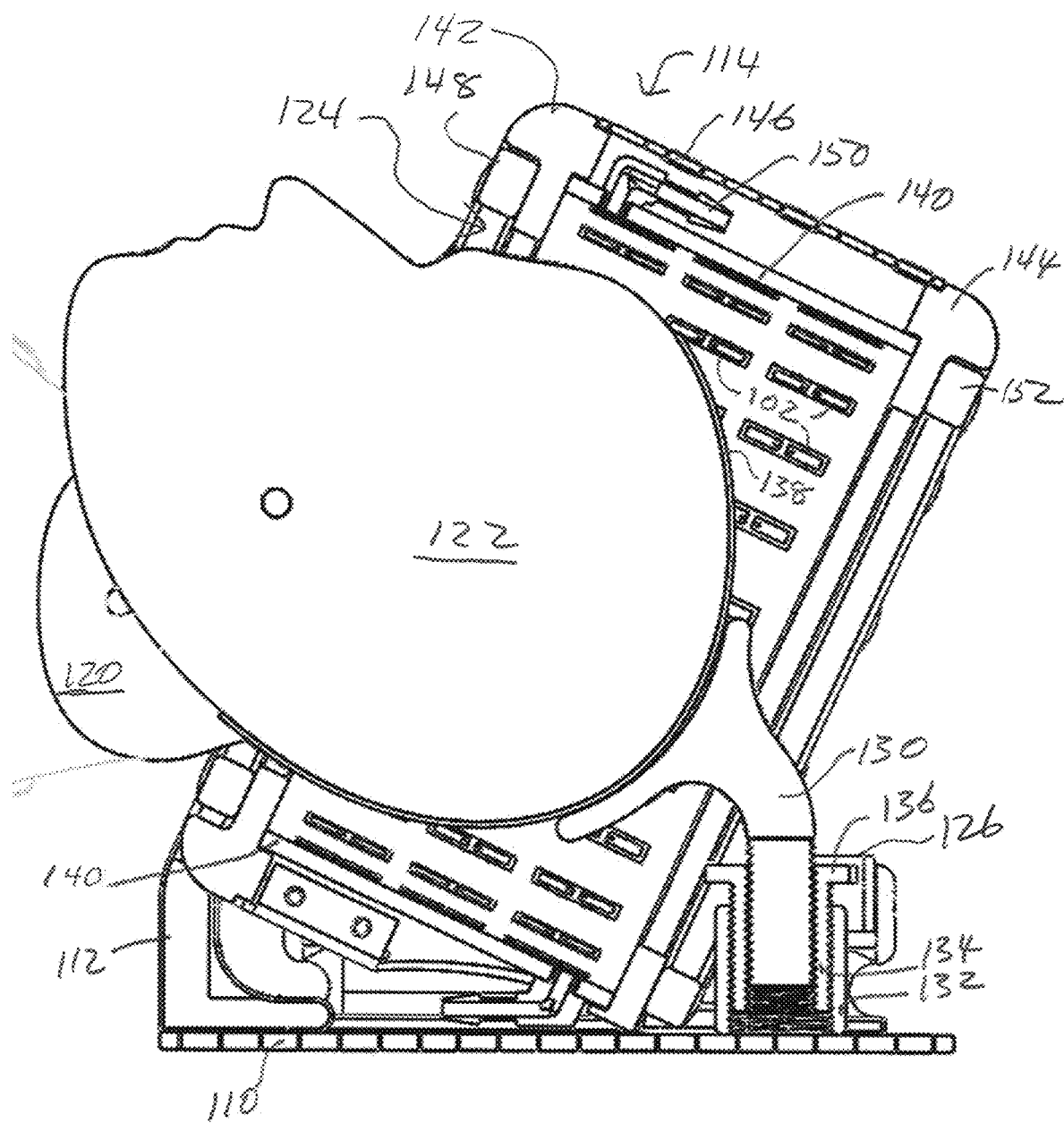
FIG. 22 is a similar vertical section as shown in FIG. 21 and showing a patient's head in the applicator.
Figure 23:
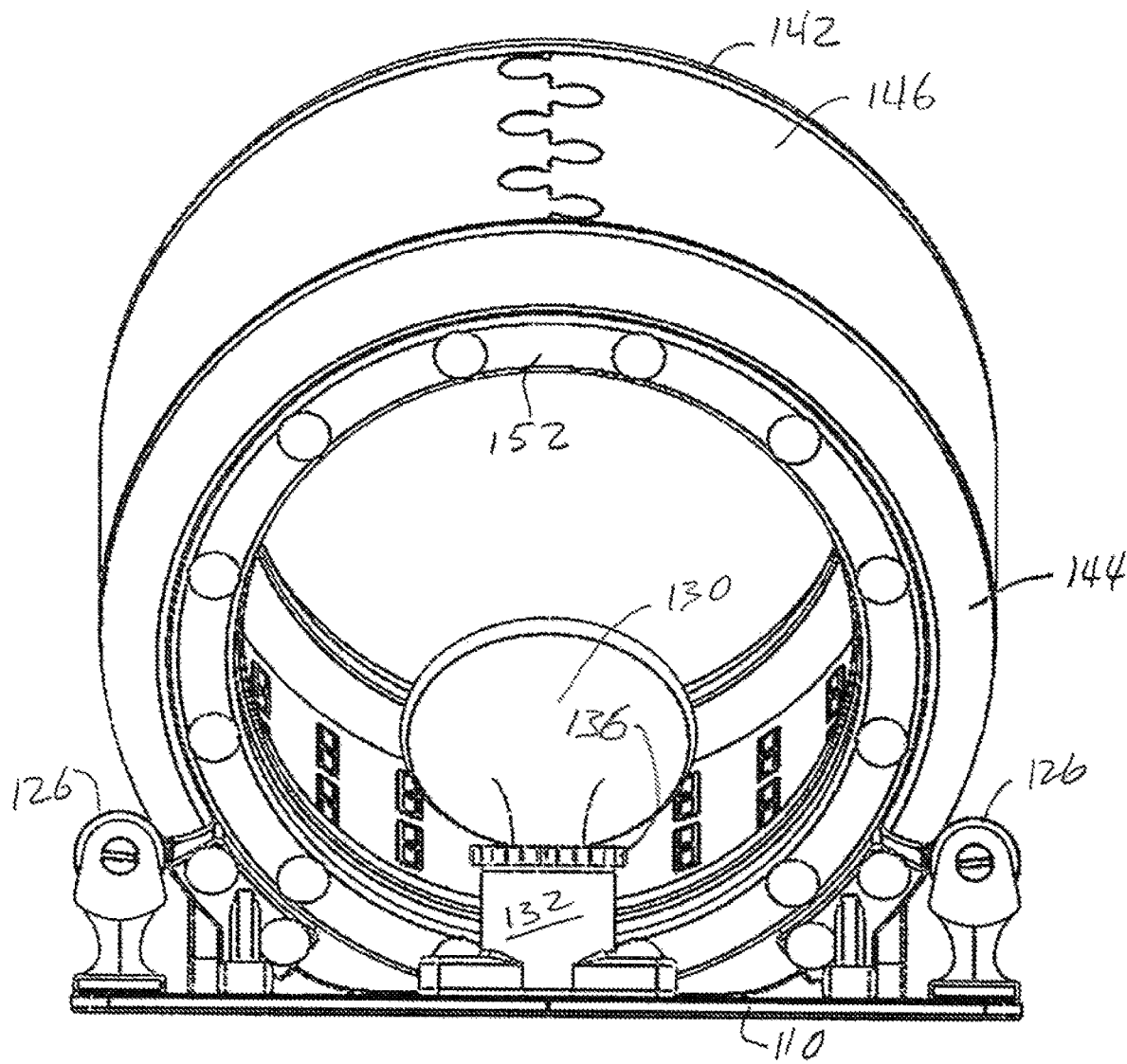
FIG. 23 is a rear elevation of an applicator of the invention as shown in FIG. 17.
Figure 24:
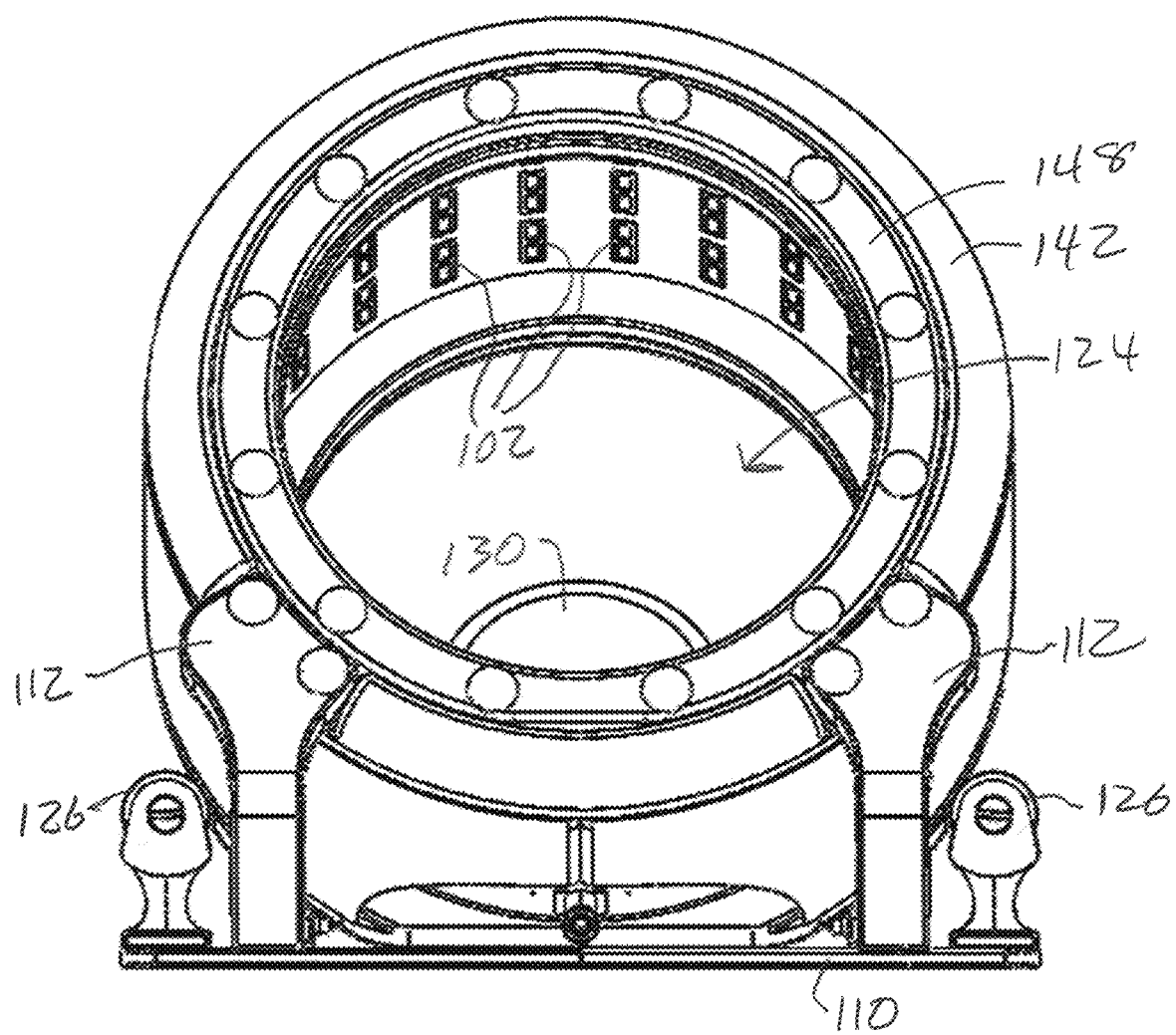
FIG. 24 is a front elevation of an applicator of the invention as shown in FIG. 17.
Figure 25:
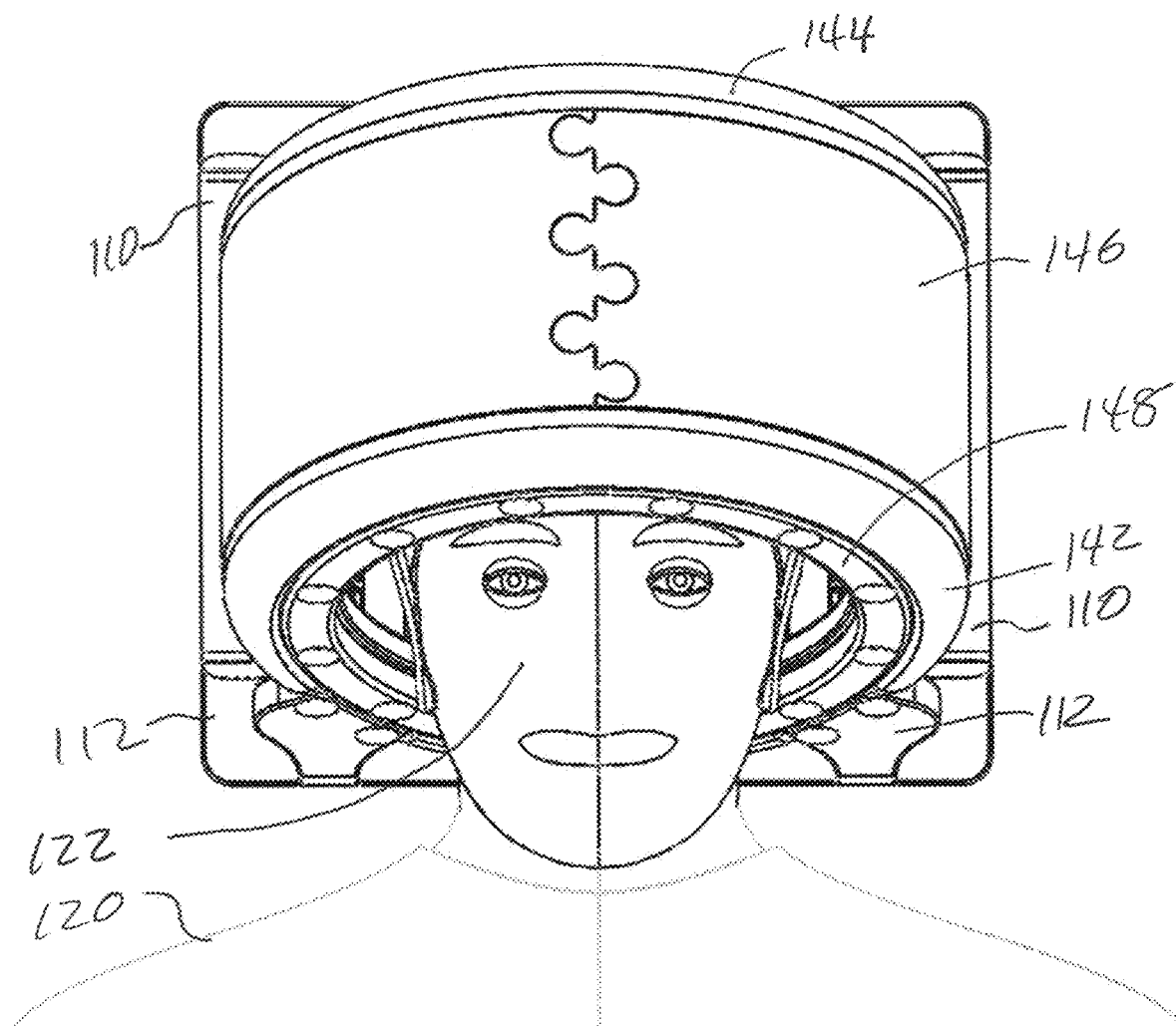
FIG. 25 is a top view of an applicator of the invention as shown in FIG. 17.

As visible in FIGS. 17, 21, 22, 23, and 24, an adjustable patient head rest 130 is adjustably secured to base 110 to support the patient's head 122 within opening 124 of antenna support housing 114. Internally threaded, cylindrical head rest mount 132 is secured to and extends upwardly from base 110 with adjustment insert 134, having a top flange 136, screwed into cylindrical head rest mount 132. Patient head rest 130 is screwed into adjustment insert 134. The mating threads of the cylindrical head rest mount 132, adjustment insert 134, and patient head rest 130 are arranged so that rotation of adjustment insert 134 in one direction will move adjustment insert 134 with respect to cylindrical head rest mount 132 in an upward direction with respect to base 110 and will also move patient head rest 130, if held against rotation with the adjustment insert 134, in the same upward direction with respect to base 110. Opposite rotation of adjustment insert 134 will move adjustment insert 134 and patient head rest 130 when held against rotation, in the opposite, downward direction with respect to base 110. FIG. 21 shows adjustment insert 134 and patient head rest 130 in lowest downward position while FIG. 22 shows adjustment insert 134 and patient head rest 130 in a partially elevated position. As shown in FIG. 22, the patient's head 122 may have a thin cap material 138 thereon. With the patient's head inserted into opening 124 of antenna support housing 114 and resting on, patient head support 130, adjustment insert 134 may be rotated by means of flange 136 to raise or lower head rest 130 to thereby adjust the position of the patient's head in antenna support housing 114.

Figure 26:
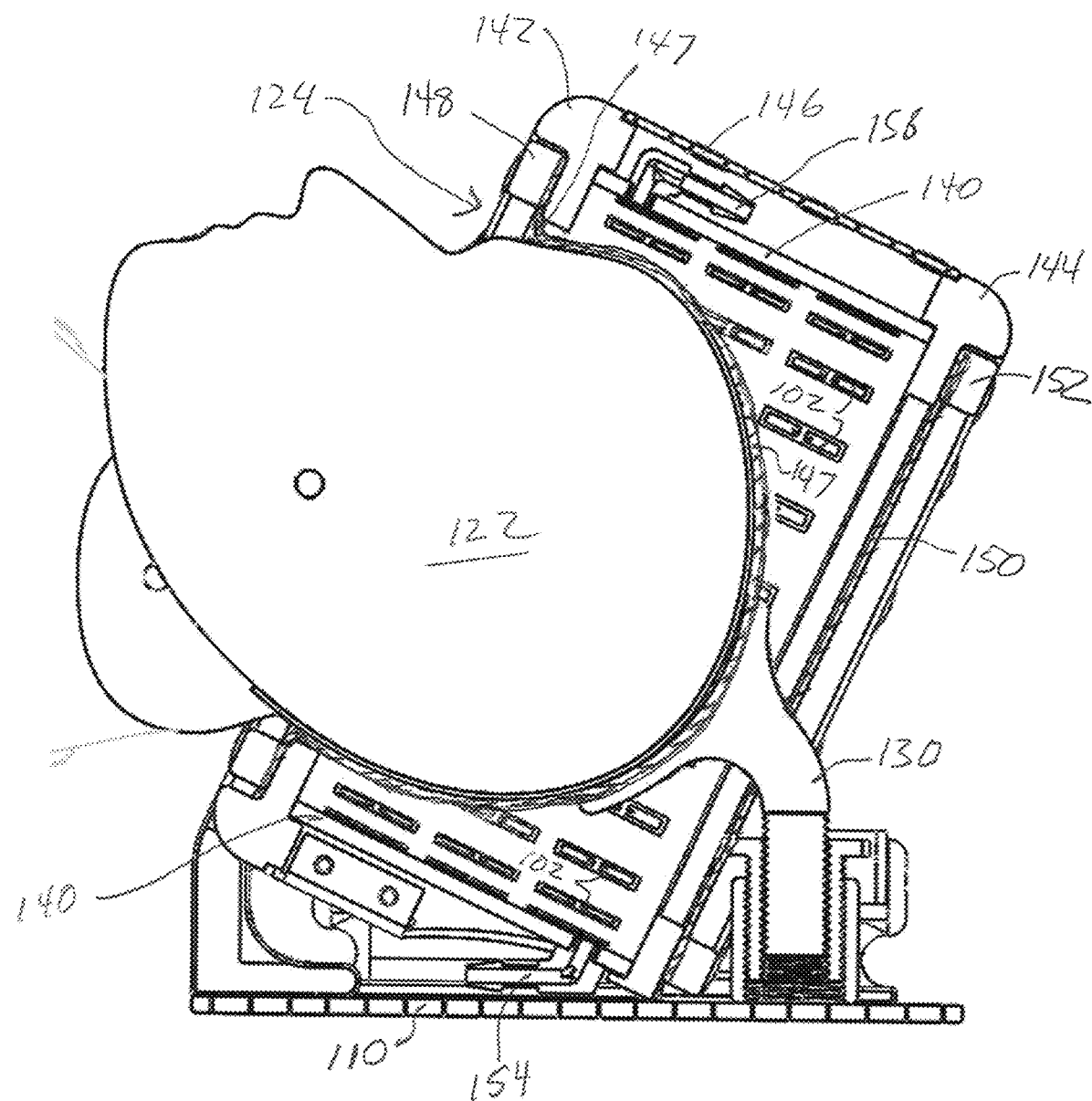
FIG. 26 is a vertical section similar to that of FIG. 21 and showing an embodiment of a bolus in the applicator.

Antenna support housing 114 may be constructed in any suitable manner to support a cylindrical antenna support surface 140 upon which the antennas 102 cattle mounted. For example, antenna support housing 114 may include a front cylindrical member 142 and a similar back cylindrical member 144 with cylindrical antenna support surface 140 secured therebetween. The connection of the cylindrical antenna support surface 140 to the front and back cylindrical members 142 and 144 should be fluid tight so that a bolus media, such as deionized water, within the cylindrical antenna support surface 140 will not leak out along the edges of the cylindrical antenna support surface 140. A cylindrical outer shell 146 secured between the front and back cylindrical members 142 and 144 forms the outer surface of the antenna support housing 114. Although not shown in FIGS. 17-25 so as not to hide the detail, a bolus is formed inside the antenna support housing 114 in opening 124 so that the head of the patient will fit within the bolus when the head of the patient is positioned in opening 124 and so that the bolus can be filled with bolus media and the bolus will contact the head of the patient when inserted into opening 124. FIG. 26 is similar to FIG. 22 showing the head 122 of the patient in the opening 124, and shows a front flexible bolus membrane 147 with edges secured between front bolus holding ring 148 and front cylindrical member 142 and back flexible bolus membrane 150 with edges secured between back bolus holding ring 152 and back cylindrical member 144. Head support 130 extends through back bolus membrane 150 and is sealingly secured thereto. Front flexible bolus membrane 146 is configured to accept a patient's head 122 therein when inserted into opening 124. Bolus media, such as deionized water, is pumped through a supply tube, not shown, connected to tube connector fitting 154 or 156 to fill the bolus space between the antennas mounted by the cylindrical antenna support surface 140 and the head 122 of the patient. Bolus media can be drained from the bolus through tube connector fitting 154 or 156. If the bolus media is circulated through the bolus during treatment, such as for cooling purposes, it has been found beneficial to insert the fluid from lower connector fitting 154 to help remove any bubbles that may form in the bolus.

Figure 27:
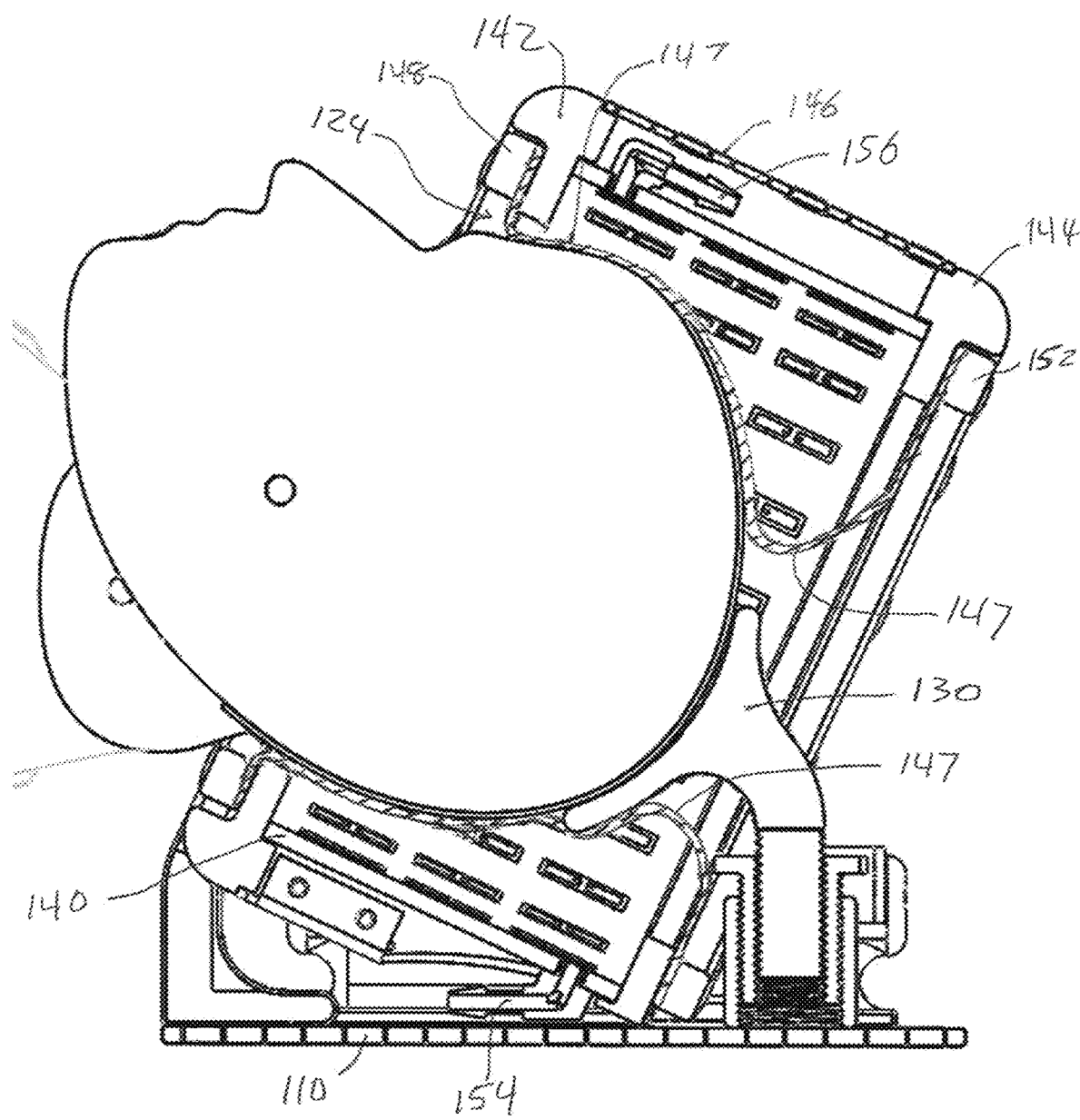
FIG. 27 is a vertical section similar to that of FIG. 26 and showing an second embodiment of a bolus in the applicator.

Rather than the bolus arrangement show in FIG. 26, an alternate, and currently preferred bolus arrangement is shown in FIG. 27, wherein the bolus forms a ring around the patient's head and has a through opening in which the patient's head is positioned. The bolus is formed of a single piece of flexible bolus membrane material 147 with the front edge of the flexible bolus membrane material 147 secured around the front of applicator opening 124 between front bolus holding ring 148 and front cylindrical member 142 and the back edge of the flexible bolus membrane material 147 secured around the back of applicator opening 124 between back bolus holding ring 152 and back cylindrical member 144. In this embodiment, the patient head rest 130 is not inside the bolus and the bolus does not surround the top of the patient's head. The patient's head can protrude out the back of the bolus if desired.

The illustrated embodiment of FIGS. 21-27 includes three rings of dipole antennas mounted by the cylindrical antenna support surface 140 with twenty four antennas in each ring for a total of 72 antennas. These 72 dipole antennas can be activated by 72 separate EMR (microwave) power channels so each can be independently controlled, or these antennas can be activated in local antenna groups that are driven by a common power channel. Fewer power control channels reduces cost and complexity for the implementation of this system. However, the use of too few power control channels will result in the creation of secondary focus hot spots within the brain and head tissues. The optimization of the balance of reduced complexity and adequate number of power channels to minimize hot spots away from the primary focus must comply with the novel design techniques outlined in this disclosure. The importance for the proper design is to minimize phase variations along the tissue surface that contribute to these hot spots. The preferred embodiment uses a fixed relative phase difference between the outer ring antennas in association to the antenna lying between them in the central ring. This would thereby allow control of a 72 antenna array with 24 channels that contained independent power and phase controls for each antenna group. This is a practical control option. However, it has been determined that the design can be further simplified by a 12 channel system, thereby an antenna grouping of two parallel antennas in the central ring is combined with two antennas from each of the two outer antenna rings providing an antenna grouping of 6 antennas that would be driven by a common EMR power and phase controlled channel. The single power input would use a power splitter transmission line network to divide the power to 12 equal channels to provide $1/12^{th}$ of the input power to each of the 6 antennas. The size of the array diameter in relation to the typical range of adult head sizes allows a 12 channel system to be a generally preferred embodiment.

Figure 28:
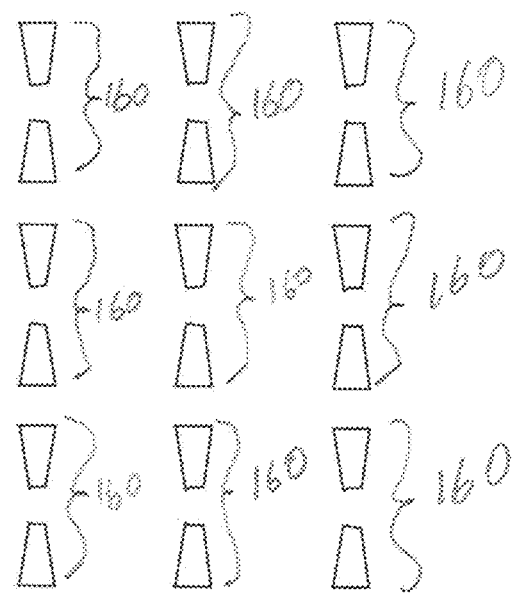
FIG. 28 is a schematic view of an antenna array showing nine dipole antennas.
Figure 29:
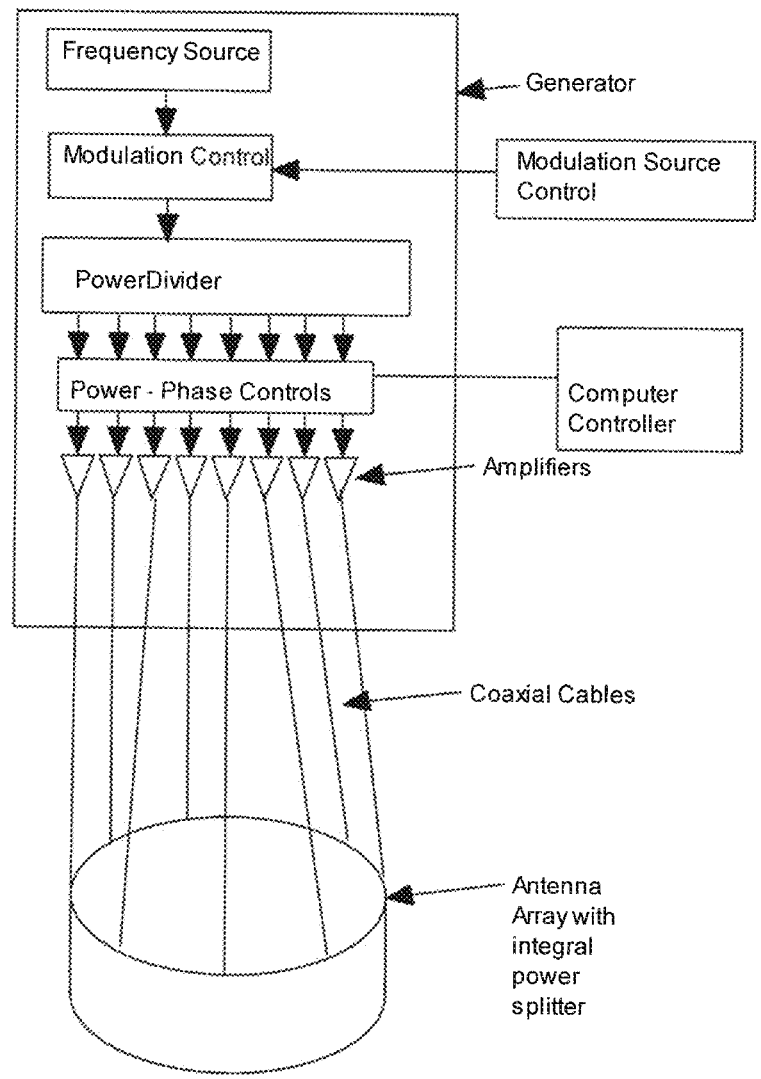
FIG. 29 is a system diagram of a control system for powering the array of FIG. 28.

There are some conditions where the diameter of the antenna array can also adequately control the hot spots away from the primary focus using an 8 channel power control system. This is provided by each of the power channels to provide EMR power to a group of antennas comprised of 3 neighboring antennas from each of the three antenna rings. For this embodiment, the common input power channel would be connected to a 9 way power divider transmission line network to provide $1/9^{th}$ of the input power to each of the antennas in the grouping. For this embodiment the power division network would provide equal power and a fixed relative phase for the antennas within the 9 antenna grouping. Typically the antennas in the outer rings relative to those in the central ring have an additional phase delay of typically 50 degrees that is provided by the transmission line delays within the power splitter network. FIG. 28 shows such an array of 9 dipole antennas 160 with 3 dipole antennas 160 stacked end to end and three of these stacked end to end groups positioned side by side to all be driven by a single microwave power input where these are all connected to the single power input using a microstrip power divider. FIG. 29 shows a system diagram for driving eight of these separate dipole antenna arrays of 9 dipole antennas each as shown in FIG. 28. The single power signal to the antennas is generated by the frequency source. This power signal can by sent through a modulation control that can be operated to modulate the power signal to the antennas, if desired. The power signal, either with or without modulation, is connected to the power divider which divides the power signal into a number of separate power signals or channels, one separate power signal or channel for each separate antenna array. FIG. 29 shows the power signal split into eight separate power signals or channels with each of the separate power signals or channels being sent through a separate phase control and separate amplifier to the antenna arrays. In FIG. 29, the eight amplifiers each allow control of the power level and the relative phase of the power signal or channel sent to one of the eight arrays. The operation of the system would interface with the operator via a computer control.

Figure 30:
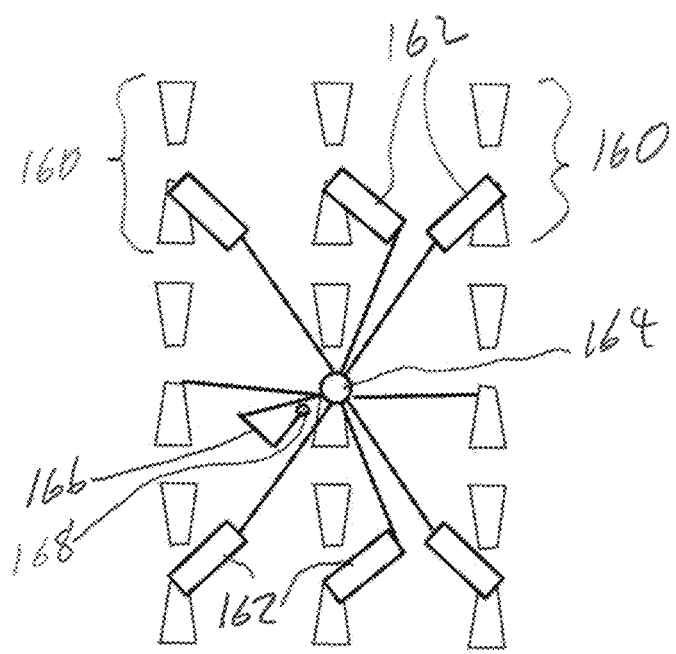
FIG. 30 is a wiring diagram for an embodiment of the array of FIG. 28.

FIG. 30 shows one of the arrays as shown in FIG. 28 and how the active stripling conductor paths can be distributed to one side of the dipoles for a 9 dipole power splitter where the thicker lines 162 show the microstrip paths which are placed on a dielectric circuit card with a ground copper layer on the opposite side of the microstrip pc board. The dipole orientation is represented with the thinner lines to demonstrate the corresponding alignment between the power splitter striplines and the dipole feed points. The feed point of the dipole elements that are not shown connected to these striplines would be connected to the copper ground plane layer. This allows all the dipoles to be connected to a single power input point, here shown as terminal 164, with an equal division of the power to each of these 9 dipoles for the 8 channel control system capability. Line 166 extends through the microstrip pc board as at 168 to connection with the dipole antenna shown behind the terminal 164.

Figure 31:
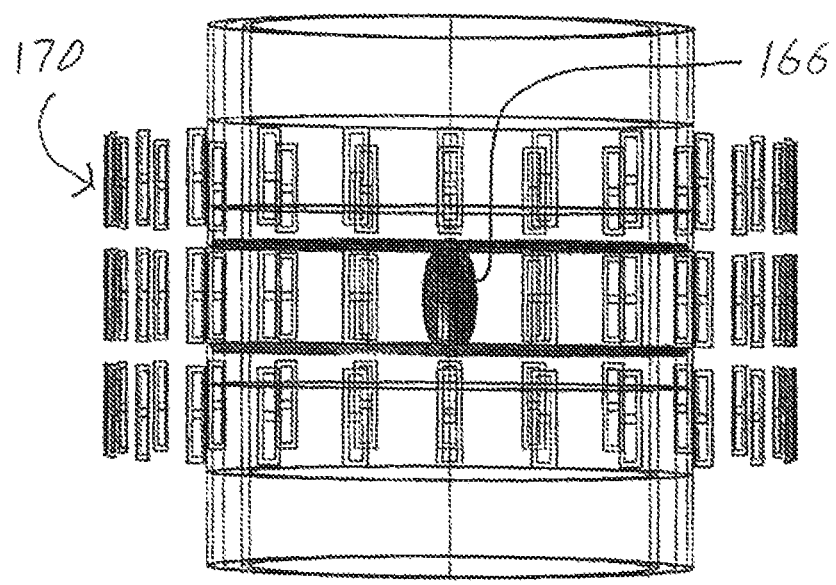
FIG. 31 is a schematic showing of a heated focus area in an applicator of the invention.

Various sizes of applicators can be used to keep within the guidelines of the invention. The size of a human brain is generally between about 13 and 16 cm with the head size containing the brain generally between about 15 and 18 cm. The bolus should generally space the antennas at least about two cm from the head around the head so the cylindrical antenna support surface 140 in the applicator should generally be of a diameter at least about four cm larger than the head. Applicator sizes of between 22 cm and about 30 cm are generally desirable. FIG. 31 shows a representation of an applicator with diameter of 26 cm represented by the circle 170 of antennas and a bolus length of 13 cm. A central heated focal zone is shown at 166. FIGS. 32-38 show the results, using a COMSOL based modeling program developed by the inventors, of the SAR (specific absorption rate) of the radio frequency energy from the radio frequency signal, which is indicative of the heating in a tissue model representing the human brain within a human head within the bolus of a radio frequency annular array hyperthermia system as shown in FIGS. 15-27. The COMSOL modeling program provides color patterns within a desired tissue area with different colors representing the SAR at various locations within the tissue area. FIGS. 32-38 are representations of such color patterns showing the outlines of the relative percentage specific SAR areas in the tissue model. These lines are referred to as the relative percentage power density or SAR (specific absorption rate) contour lines. In generating a desired heated focal zone in tissue, it is desired that substantially all of the tissue within the heated focal zone have a relative SAR (specific absorption rate or absorbed power per unit mass) of at least 50%. Also in generating this desired heated focal zone in tissue, it is important that substantially all of the tissue outside of the desired heated focal zone have a relative SAR of less than 50%. Generally in FIGS. 32-35, the large circle indicated by reference number 170 in each Fig. represents the outer dielectric bolus boundary formed by the cylindrical antenna support surface supporting the antennas, with the antennas shown as forming this circle. The first circle inside the bolus boundary, indicated by reference number 174 in each Fig., represents the inner bolus boundary against the outer surface of the head of the patient. The next lighter circle inward, indicated by reference number 176, represents a model of the cervical spinal fluid (CSF) that is between the skull and the brain. This material has a higher electrical conductivity which results in a thin region of higher SAR at level of about 40%. The inner edge of this circle would represent the outer edge of the brain within the head. The light inner area represents the heated focal zone, which in FIGS. 31-35 is a central heated focal zone. The indicated central heated focal zone 178 shows an SAR ranging from 40 to 100%. All the zones between the heated central focus zone 178 and the CSF ring 176 remained between 0 to 30% SAR.

Figure 32:
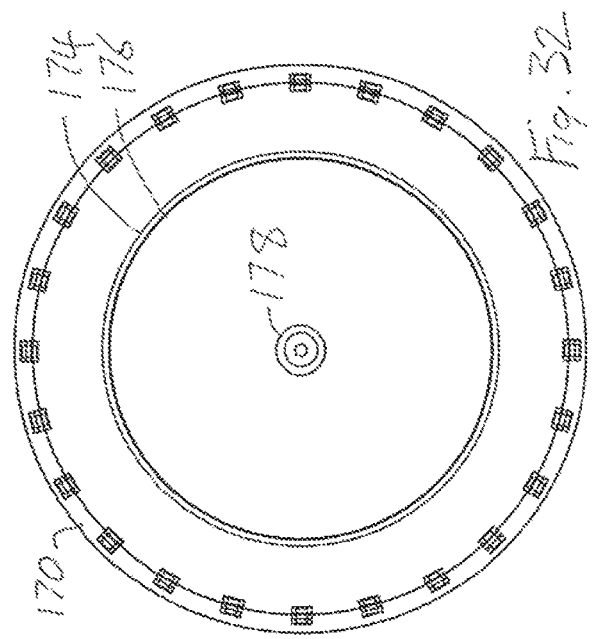
FIGS. 32-38 are simulations of heating patterns produced by the applicator of the invention in brain tissue.
Figure 33:
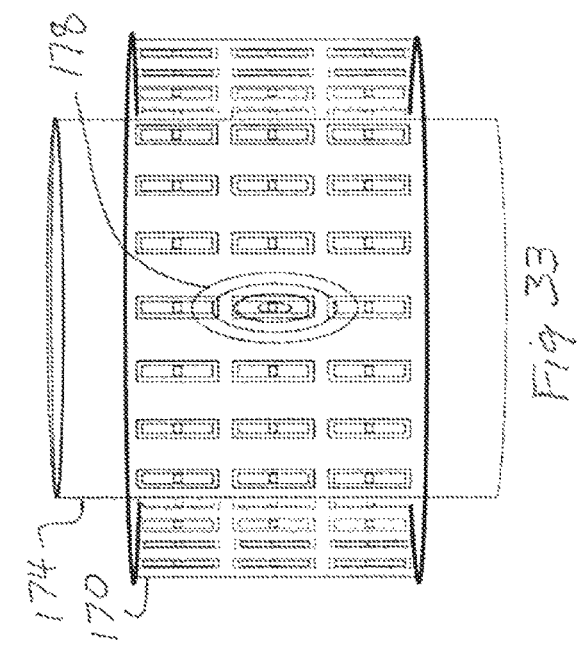
Figure 34:
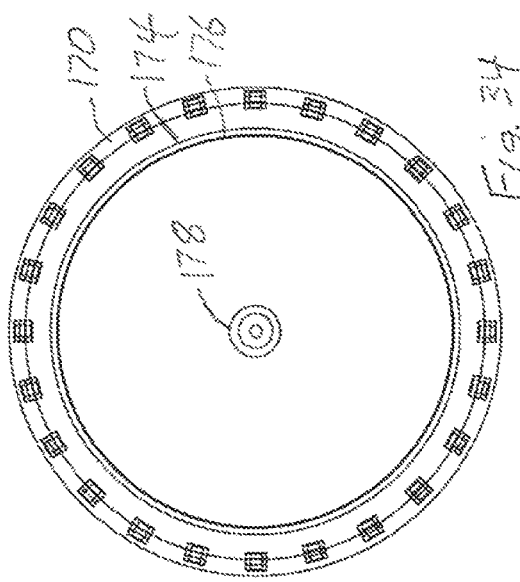
Figure 35:
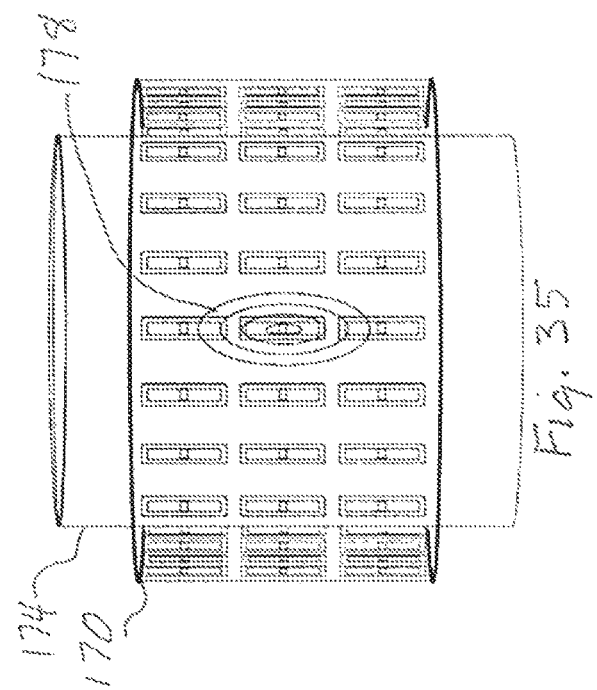

FIG. 32 is a radial cross section of an applicator with diameter of 26 cm represented by the circle 170 of antennas and a bolus length of 13 cm. The heated focal zone is shown at 178. FIG. 33 is a longitudinal cross section of the same applicator. FIG. 34 is a radial cross section of a similar applicator with diameter of 22 cm represented by the circle 170 of antennas and a bolus length of 13 cm. The heated focal zone is shown at 178. FIG. 35 is a longitudinal cross section of the same 22 cm diameter applicator. FIGS. 34 and 35 show that there is a central SAR focus maintained with an applicator diameter of 22 cm as compared to an applicator diameter of 26 cm. This comparison shows less energy absorption in the superficial skin and a slightly more focused pattern in the ZX plane for the 26 cm diameter. The lower SAR values can also be depicted in the $SAR_{50\%}$ isovolumes shown at the end. These results are favourable from a practical perspective, since the 26 cm applicator permits a 4 cm water thickness around the average human head (18 cm diameter), whereas the 22-cm applicator only permits 2 cm water thickness. However, favorably, this shows that substantially the same focus can be achieved with both of these diameters. These Figs. show the same central focus that is the light to dark zone from 40 to 100% SAR. The dark areas elsewhere outside the central focus are 0 to 30% SAR. The small lighter zones to the two sides from the central focus could be a thin region of the CSF.

Figure 36:
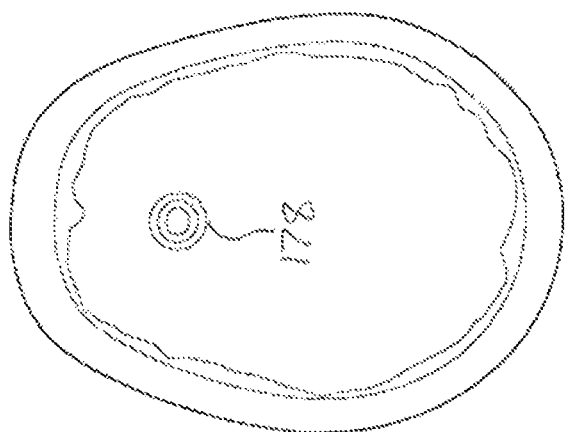
Figure 37:
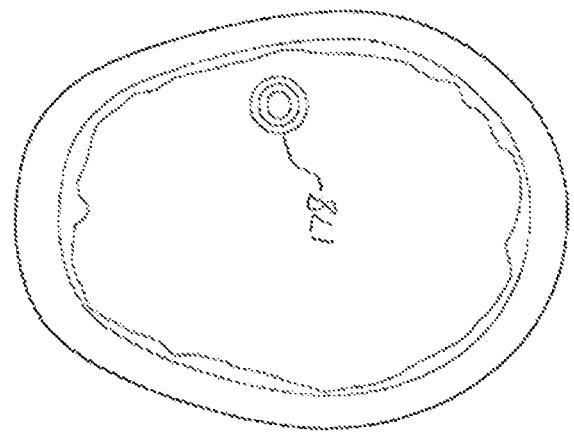
Figure 38:
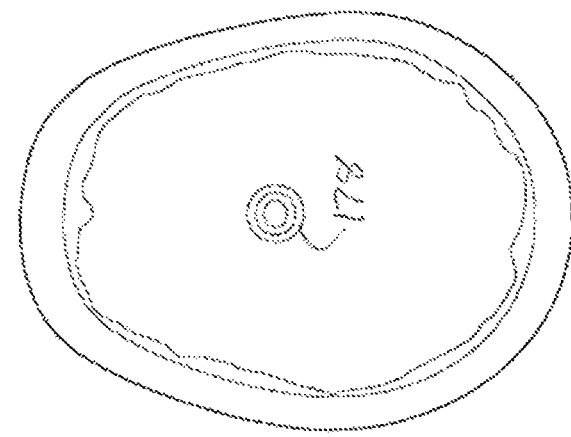

FIGS. 36, 37, and 38 show further heating patterns for brain tissue and show how phase changes for the modeled antennas can move the heated focal zone to different focal positions. FIG. 36 shows a focus in the center of the brain, FIG. 37 show the focus targeted at 3 cm from the center of the brain to the lateral side, and FIG. 38 shows the focus set at 3 cm toward the front side of the head within the brain. Note each of these show the heated focal zone being an SAR zone from 40 to 100% of the maximum SAR within the head model. The regions outside of the heated focal zone are shown to be between 0 and 40%. The head model includes white matter, grey matter, central ventricle which is filled with CSF, outer CSF between the brain and the skull, the skull is the outer dark region. Note fat and skull tissue are similar in electrical properties so the model of the outer dark zones include what would also be fatty tissue together with the skull bone.

A further aspect of the invention, and as shown in the system diagram of FIG. 29, is to have a common microwave source that can be modulated as a common input to each of the microwave power channels, where the modulation is similar to global communications system modulation with amplitude modulation, or any other type of modulation desired. This would enable non-thermal effects due to the modulation effects. The system would also be able to switch off the modulation to create more tissue heating to create hyperthermia and thermal effects such as heat shock proteins, increased blood flow, and increased thermal related effects. In the generator the common microwave (EM) frequency source that is divided within the generator to be amplified, power controlled, and phased controlled will have the same modulation state. The unique and novel approach of this system configuration is that the highly focused microwave fields within the brain will be capable to apply the heating of exposure power to a very localized position within the brain. The system is designed to allow under the physician's guidance the selection of the type of modulation to be used or the selection of an unmodulated reference signal that is amplified. This unique ability to apply a localized region of exposure in the brain to the microwave power that is either continuous wave or modulated provides a significant benefit for selectively adapt the therapy approach to the condition to be treated in the brain. Other methods use exposure of the entire body or head for such effects. The more localized energy focus allows a new way to deliver such microwave (EM) energy to the regions of the brain most responsible for the effects and the disease condition.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A radio frequency annular phased array hyperthermia system to provide a heated focal zone of diameter of about 3 cm or less in a selected position in a tissue mass, said hyperthermia system comprising:
   a bolus adapted to be positioned around the tissue mass in which the heated focal zone is to be provided to form an interface with the outer surface of the tissue mass, said bolus having a size and having a bolus media therein with a bolus media dielectric constant;
   a plurality of radio frequency energy radiator applicators positioned in three rings around the tissue mass in which the heated focal zone is to be provided and spaced by the bolus media a distance from the surface of the tissue mass, each radio frequency energy radiator applicator operable to radiate radio frequency signals of a predetermined frequency of 900 MHz or above through the bolus media into the tissue mass wherein the electric field of the radiated signals from each radio frequency energy radiator applicator are superimposed in a controlled manner to produce the heated focal zone in the selected position in the tissue mass, each radio frequency energy radiator applicator having a center and spaced substantially equally from respective adjacent radio frequency energy radiator applicators circumferentially around a respective ring of the three rings,
   wherein
   the radio frequency energy radiator applicators are spaced, the bolus is sized, and the bolus media dielectric constant is selected so that the distance between centers of respective adjacent radio frequency energy radiator applicators around a respective ring is no greater than 0.8 of the wavelength of the radio frequency signal of the predetermined frequency in the bolus media and the difference in phase at a bolus-tissue mass interface point between a radiated signal traveling through the bolus between the center of a radio frequency energy radiator applicator and the center of the tissue mass and a signal traveling through the bolus to that point from the center of an adjacent radio frequency energy radiator applicator is no more than 135 degrees, and
   the three rings of the radio frequency energy radiator applicators are spaced along an axis of the tissue mass so that respective radio frequency energy radiator applicators in each ring are aligned and have a longitudinal separation distance between adjacent aligned radio frequency energy radiator applicators no greater than 0.8 of the wavelength of the radio frequency signal of the predetermined frequency in the bolus media and the difference in phase at a bolus-tissue mass interface between signals from the center of aligned stacked radio frequency energy radiator applicators mid way between the rings is no more than 125 degrees.

2. A radio frequency annular phased array hyperthermia system to provide a heated focal zone in a selected position in a tissue mass according to claim 1, wherein the size of the bolus is determined by an outside diameter of the bolus and wherein the outside diameter of the bolus is between 22 cm and 30 cm.

3. A radio frequency annular phased array hyperthermia system to provide a heated focal zone in a selected position in a tissue mass according to claim 2, wherein the bolus media is deionized water with a dielectric constant of about 78.

4. A radio frequency annular phased array hyperthermia system to provide a heated focal zone in a selected position in a tissue mass according to claim 1, wherein the total number of radio frequency energy radiator applicators is 48 evenly divided between the three rings.

5. A radio frequency annular phased array hyperthermia system to provide a heated focal zone in a selected position in a tissue mass according to claim 1, wherein the total number of radio frequency energy radiator applicators is 72 evenly divided between the three rings.

6. A radio frequency annular phased array hyperthermia system to provide a heated focal zone in a selected position in a tissue mass according to claim 5, wherein the 72 energy radiator applicators are divided into eight arrays of nine energy radiator applicators each and power to each array is independently controlled.

7. A radio frequency annular phased array hyperthermia system to provide a heated focal zone in a selected position in a tissue mass according to claim 1, wherein the power supplied to the radio frequency energy radiator applicators, when operated, can be modulated.

8. A radio frequency annular phased array hyperthermia system to provide a heated focal zone in a selected position in a tissue mass according to claim 1, wherein the predetermined frequency is between 900 MHz. and 930 Mhz.

9. A radio frequency annular phased array hyperthermia system to provide a heated focal zone in a selected position in a tissue mass according to claim 1, wherein the predetermined frequency is 915 MHz.

10. A radio frequency annular phased array hyperthermia system to provide a heated focal zone of diameter of about 3 cm or less in a selected position in a human brain tissue mass, said hyperthermia system comprising:
   a bolus adapted to be positioned around the head of a patient in whose brain the heated focal zone is to be provided to form an interface with the head, said bolus having a size and having a bolus media of deionized water therein with a bolus media dielectric constant of about 78;
   a plurality of at least 48 radio frequency energy radiator applicators positioned in three rings of at least 16 radio frequency energy radiator applicators in each ring around the head of the patient in whose brain the heated focal zone is to be provided and spaced by the bolus media a distance from the surface of the head, each radio frequency energy radiator applicator operable to radiate radio frequency signals of a predetermined frequency greater than 900 MHz through the bolus media into the head and brain of the patient wherein the electric field of the radiated signals from each radio frequency energy radiator applicator are superimposed in a controlled manner to produce the heated focal zone of 3 cm or less in the selected position in the brain, each radio frequency energy radiator applicator having a center and spaced substantially equally from respective adjacent radio frequency energy radiator applicators circumferentially around a respective ring of the three rings;

wherein the radio frequency energy radiator applicators are spaced, the bolus is sized, and the bolus media dielectric constant is selected so that the distance between centers of respective adjacent radio frequency energy radiator applicators around the a respective ring is no greater than 0.8 of the wavelength of the radio frequency signal of the predetermined frequency in the bolus media and the difference in phase at a bolus-head interface point between a radiated signal traveling through the bolus between the center of a radio frequency energy radiator applicator and the center of the head and a signal traveling through the bolus to that point from the center of an adjacent radio frequency energy radiator applicator is no more than 135 degrees, and the three rings of the radio frequency energy radiator applicators are spaced along an axis of the head so that respective radio frequency energy radiator applicators in each ring are aligned and have a longitudinal separation distance between adjacent aligned radio frequency energy radiator applicators no greater than 0.8 of the wavelength of the radio frequency signal of the predetermined frequency in the bolus media and the difference in phase at a bolus-head interface between signals from the center of aligned stacked radio frequency energy radiator applicators mid way between the rings is no more than 125 degrees.

11. A radio frequency annular phased array hyperthermia system to provide a heated focal zone of diameter of about 3 cm or less in a selected position in a human brain tissue mass according to claim 10, wherein the power supplied to the radio frequency energy radiator applicators, when operated, can be modulated.

12. A method of producing a heated focal zone of a desired size of about 3 cm or less in a selected position in a human brain tissue mass, comprising the steps of:

arranging three rings of radio frequency energy radiator applicators of at least 16 applicators each around and spaced by a bolus media from the head of a patient containing the brain tissue mass in which the heated focal zone is to be produced, each radio frequency energy radiator applicator operable to radiate radio frequency signals of a predetermined frequency of at least 900 MHz through the bolus media into said brain tissue mass in a manner wherein the electric field of the radiated signals from each radio frequency energy radiator applicator are superimposed in a controlled manner to produce the heated focal zone in the selected position in the brain tissue mass, each radio frequency energy radiator applicator having a center and spaced substantially equally from respective adjacent radio frequency energy radiator applicators circumferentially around a respective ring of the three rings and the bolus media having a dielectric constant and an interface with the outer surface of the head, and the three rings of the radio frequency energy radiator applicators are spaced along an axis of the head so that respective radio frequency energy radiator applicators in each ring are aligned;

arranging the spacing of the radio frequency energy radiator applicators, the bolus size, and the bolus media dielectric constant so that the distance between centers of respective adjacent radio frequency energy radiator applicators around a respective ring is no greater than 0.8 of the wavelength of the radio frequency signal of the predetermined frequency in the bolus media and the difference in phase at a bolus-head interface point between a radiated signal traveling through the bolus between the center of a radio frequency energy radiator applicator and the center of the head and a signal traveling through the bolus to that point from the center of an adjacent radio frequency energy radiator applicator is no more than 135 degrees;

arranging the spacing of the three rings of the radio frequency energy radiator applicators along the axis of the head so that respective radio frequency energy radiator applicators in each ring are aligned and have a longitudinal separation distance between adjacent aligned radio frequency energy radiator applicators no greater than 0.8 of the wavelength of the radio frequency signal in the bolus media and the difference in phase at the bolus-head interface between signals from the center of aligned stacked radio frequency energy radiator applicators mid way between the rings is no more than 125 degrees; and and operating the radio frequency energy radiator applicators to radiate radio frequency signals of the predetermined frequency on either a continuous wave radio frequency energy basis, a modulated radio frequency energy basis, or a combination thereof.

13. A method of producing a heated focal zone of a desired size of about 3 cm or less in a selected position in a human brain tissue mass, according to claim 12, wherein the human brain tissue mass has a malignant tumor therein in a tumor location, wherein heat treatment of the malignant tumor is thought to be beneficial, wherein the selected position for the heated focal zone is the tumor location, and wherein the radio frequency energy radiator applicators are operated to produce the heated focal zone at the tumor location to thereby heat and treat the tumor.

14. A method of producing a heated focal zone of a desired size of about 3 cm or less in a selected position in a human brain tissue mass, according to claim 12, wherein the human brain tissue mass has a fluid filled region therein in a fluid filled location, wherein heating of the fluid in the fluid filled region is thought to be beneficial, wherein the selected position for the heated focal zone is the fluid filled location, and wherein the radio frequency energy radiator applicators are operated to produce the heated focal zone in the fluid filled location to thereby heat the fluid in the fluid filled location.

15. A method of producing a heated focal zone of a desired size of about 3 cm or less in a selected position in a human brain tissue mass, according to claim 14, wherein the fluid filled region is a substantially circular cavity filled with body fluids after resection of a malignant tumor from the brain.

16. A method of producing a heated focal zone of a desired size of about 3 cm or less in a selected position in a human brain tissue mass, according to claim 12, wherein the human brain tissue mass has a diseased tissue region therein in a diseased tissue location, wherein heating of the diseased tissue in the diseased tissue region is thought to be beneficial, wherein the selected position for the heated focal zone is the diseased tissue location, and wherein the radio frequency energy radiator applicators are operated to produce the heated focal zone in the diseased tissue location to thereby heat the diseased tissue in the diseased tissue location.

17. A method of producing a heated focal zone of a desired size of about 3 cm or less in a selected position in a human brain tissue mass, according to claim 16, wherein the diseased tissue region is in the hippocampus portion of the human brain tissue mass, wherein application of radio frequency energy to the diseased tissue in the diseased tissue region is thought to be beneficial, wherein the selected position for the heated focal zone is the diseased tissue region in the hippocampus portion of the human brain tissue mass, and wherein the radio frequency energy radiator applicators are operated to produce the heated focal zone in the diseased tissue region to thereby apply radio frequency energy the diseased tissue in the diseased tissue region.

18. A method of producing a heated focal zone of a desired size of about 3 cm or less in a selected position in a human brain tissue mass, according to claim 12, wherein the human brain tissue mass has a region therein where heating is thought to be beneficial, wherein the selected position for the heated focal zone is the region where heating is thought to be beneficial, and wherein the radio frequency energy radiator applicators are operated to produce the heated focal zone in the region where heating is thought to be beneficial.

\* \* \* \* \*